(12) United States Patent
Ryding et al.

(10) Patent No.: US 9,249,418 B2
(45) Date of Patent: Feb. 2, 2016

(54) USE OF PLANT PROMOTERS IN FILAMENTOUS FUNGI

(71) Applicant: BP CORPORATION NORTH AMERICA INC., Houston, TX (US)

(72) Inventors: Nicholas J. Ryding, San Diego, CA (US); Wenqi Hu, San Diego, CA (US); Biyu Li, San Diego, CA (US)

(73) Assignee: BP Corporation North America Inc., Houston, TX (US)

( * ) Notice: Subject to any disclaimer, the term of this patent is extended or adjusted under 35 U.S.C. 154(b) by 620 days.

(21) Appl. No.: 13/665,462

(22) Filed: Oct. 31, 2012

(65) Prior Publication Data

US 2013/0109054 A1     May 2, 2013

Related U.S. Application Data

(60) Provisional application No. 61/553,897, filed on Oct. 31, 2011.

(51) Int. Cl.
| | |
|---|---|
| *C12N 1/14* | (2006.01) |
| *C12P 21/02* | (2006.01) |
| *C12N 15/80* | (2006.01) |
| *C12N 15/81* | (2006.01) |

(52) U.S. Cl.
CPC .............. *C12N 15/80* (2013.01); *C12N 15/815* (2013.01); *C12P 21/02* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 5,364,770 | A | 11/1994 | Berka et al. |
| 5,578,463 | A | 11/1996 | Berka et al. |
| 5,646,333 | A * | 7/1997 | Dobres et al. ................. 800/302 |
| 5,679,543 | A | 10/1997 | Lawlis |
| 6,004,785 | A | 12/1999 | Berka et al. |
| 6,103,490 | A | 8/2000 | Berka et al. |
| 6,130,063 | A | 10/2000 | Lawlis |
| 6,171,817 | B1 | 1/2001 | Berka et al. |
| 6,379,928 | B1 | 4/2002 | Berka et al. |
| 2010/0055747 | A1 * | 3/2010 | Kelemen et al. ............. 435/105 |

FOREIGN PATENT DOCUMENTS

| | | |
|---|---|---|
| WO | WO 02-00896 A2 | 1/2002 |
| WO | WO 2005-001036 A2 | 1/2005 |
| WO | WO 2009-035500 A1 | 3/2009 |

OTHER PUBLICATIONS

Churchill, et al. "Transformation of the fungal pathogen Cryphonectria parasitica with a variety of heterologous plasmids," Curr Genet, vol. 17, Jan. 1, 1990, pp. 25-31, XP001314795, table 1.
Database EMBL (Online) Nov. 7, 2006, "Hypocrea jecorina glyceraldehydes-3-phosphate dehydrogenase (GAPDH) gene, complete cds," XP002691480, retrieved from EBI accession No. EM_STD:EF043568 Database accession No. EB043568 the whole document.
Hoffman, Torsten et al. "Foreign DNA sequences are received by a wild-type strain of Aspergillus niger after co-culture with transgenic higher plants," Current Genetics, vol. 27, No. 1, Jan. 1, 1994, pp. 70-76, XP009166835, New York, NY, US ISSN: 0172-8083, p. 72, col. 1; figure 3.
Mach, Robert L. et al. "Transformation of Trichoderma reesei based on hygromycin B resistance using homologous expression signals," Current Genetics, vol. 25, No. 6, Jan. 1, 1994, pp. 567-570, XP009101507, New York, NY, US ISSN: 0172-8083, DOI: 10.1007/BF00351679.
Ryabova, "Ribosome shunting in the cauliflower mosaic virus 35S RNA leader is a special case of reinitiation of translation functioning in plant and animal systems," Genes & Development, vol. 14, No. 7, Jan. 1, 2000, p. 817, XP055052460, ISSN: 0890-9369, DOI: 10.1101/gad.14.7.817 abstract.

* cited by examiner

*Primary Examiner* — Jim Ketter
(74) *Attorney, Agent, or Firm* — DLA Piper LLP (US)

(57) ABSTRACT

The present disclosure is directed to the use of plant promoters to drive recombinant expression in filamentous fungal cells. In certain aspects, the present disclosure provides an expression cassette useful for the expression of polypeptide in filamentous fungal cells. Also provided herein, are vectors and recombinant filamentous fungal cells comprising the expression cassettes of the present disclosure, and methods of making and using the same for recombinant polypeptide expression.

83 Claims, 13 Drawing Sheets

SEQUENCE LISTING

<160> NUMBER OF SEQ ID NOS: 34

<210> SEQ ID NO 1
<211> LENGTH: 525
<212> TYPE: DNA
<213> ORGANISM: Cauliflower mosaic virus

<400> SEQUENCE: 1

```
gtcaaagatt caaatagagg acctaacaga actcgccgta aagactggcg aacagttcat    60
acagagtctc ttacgactca atgacaagaa gaaaatcttc gtcaacatgg tggagcacga   120
cacacttgtc tactccaaaa atatcaaaga tacagtctca gaagaccaaa gggcaattga   180
gacttttcaa caaagggtaa tatccggaaa cctcctcgga ttccattgcc cagctatctg   240
tcactttatt gtgaagatag tggaaaagga aggtggctcc tacaaatgcc atcattgcga   300 taaggaaag gccatcgttg aagatgcctc tgccgacagt ggtcccaaag atggaccccc   360
acccacgagg agcatcgtgg aaaaagaaga cgttccaacc acgtcttcaa agcaagtgga   420
ttgatgtgat atctccactg acgtaaggga tgacgcacaa tcccactatc cttcgcaaga   480
cccttcctct atataaggaa gttcatttca tttggagaga acacg                   525
```

<210> SEQ ID NO 2
<211> LENGTH: 903
<212> TYPE: DNA
<213> ORGANISM: Commelina yellow mottle virus

<400> SEQUENCE: 2

```
gtgcaaccac tcagacaaaa gatggcacca acaggagaca agagaatgaa tccagaaaca    60
tggaagatgg taagacagat aaaagaaaag gtgaaaaatc tccctgatct tcagttacca   120
cctaaagatt cattcatcat aatagagacg gatggttgta tgactggctg gggagccgtc   180
tgcaaatgga aaatgtcaaa gcatgatcca agaagcaccg aaagaatttg tgcctatgct   240
agtggatcat tcaatccaat aaaatcaacc atcgatgcag agattcaggc ggcaatccat   300
ggcctggata aattcaaaat ttattatctt gataaaaagg agctcataat tcgctcagac   360
tgtgaagcaa ttatcaaatt ttacaacaag acgaacgaaa ataagccgtc tagagttaga   420
tggttaacat tttcagattt cttaacaggt cttggaatca cagttacatt cgagcacata   480
gatggaaagc ataatggctt agcagatgct ctatcaagaa tgataaattt cattgtggag   540
aaaaatgatg aatctccata caggttcact tcatcagtag aggacgcact aaaggtctgc   600
aatgatgatc acggaagaaa tttgatatcc gccgtcatca atgacatcat cacagtactg   660
aggagatgaa tacttagcca tgaagtagcg tgcgaatatt acctatgcct ttattcgcag   720
cgttagtggc actgaaaggc ataaagtttg ttcgttctta tcaaaaacga atcttatctt   780
tgtaacttgg ttacccggta tgccggttcc caagctttat ttccttattt aagcacttgt   840
gtagtagctt agaaaaccaa cacaacaaca ccaagaatac tttgagtgta gtaattggtt   900
cta                                                                 903
```

<210> SEQ ID NO 3

```
<211> LENGTH: 53
<212> TYPE: DNA
<213> ORGANISM: Cauliflower mosaic virus

<400> SEQUENCE: 3
gtaccgctga aatcaccaat ctctctctac aaatctatct ctctctattt ctc         53

<210> SEQ ID NO 4
<211> LENGTH: 100
<212> TYPE: DNA
<213> ORGANISM: Trichoderma reesei

<400> SEQUENCE: 4
cctcctccct ctctccctct cgtttcttcc taacaaacaa ccaccaccaa aatctctttg   60
gaagctcacg actcacgcaa gctcaattcg cagatacaaa                        100

<210> SEQ ID NO 5
<211> LENGTH: 150
<212> TYPE: DNA
<213> ORGANISM: Trichoderma reesei

<400> SEQUENCE: 5
agctaccccg ccagactctc ctgcgtcacc aattttttc cctatttacc cctcctccct    60
ctctccctct cgtttcttcc taacaaacaa ccaccaccaa aatctctttg gaagctcacg  120
actcacgcaa gctcaattcg cagatacaaa                                    150

<210> SEQ ID NO 6
<211> LENGTH: 200
<212> TYPE: DNA
<213> ORGANISM: Trichoderma reesei

<400> SEQUENCE: 6
acgatgcggc ttctgttcgc ctgcccctcc tcccactcgt gcccttgacg agctaccccg   60
ccagactctc ctgcgtcacc aattttttc cctatttacc cctcctccct ctctccctct  120
cgtttcttcc taacaaacaa ccaccaccaa aatctctttg gaagctcacg actcacgcaa  180
gctcaattcg cagatacaaa                                               200

<210> SEQ ID NO 7
<211> LENGTH: 688
<212> TYPE: DNA
<213> ORGANISM: Trichoderma reesei

<400> SEQUENCE: 7
ggccaggtcc tgaaccctta ctactctcag tgcctgtaaa gctccgtggc gaaagcctga   60
cgcaccggta gattcttggt gagcccgtat catgacggcg gcgggagcta catggccccg  120
ggtgatttat tttttttgta tctacttctg acccttttca aatatacggt caactcatct  180
ttcactggag atgcggcctg cttggtattg cgatgttgtc agcttggcaa attgtggctt  240
tcgaaaacac aaaacgattc cttagtagcc atgcatttta agataacgga atagaagaaa  300
gaggaaatta aaaaaaaaaa aaaacaaaca tcccgttcat aacccgtaga atcgccgctc  360
ttcgtgtatc ccagtaccac ggcaaaggta tttcatgatc gttcaatgtt gatattgttc  420
ccgccagtat ggctccaccc ccatctccgc gaatctcctc ttctcgaacg cggtagtggc  480
gcgcaaattg gtaatgaccc atagggagac aaacagcata atagcaacag tggaaattag  540
tggcgcaata attgagaaca cagtgagacc atagctggcg gcctgaaaag cactgttgga  600
gaccaacttg tccgttgcga ggccaacttg cattgctgtc aggacgatga caacgtagcc  660
```

```
gaggaccgtc acaagggacg caagtgcg                                          688

<210> SEQ ID NO 8
<211> LENGTH: 40
<212> TYPE: DNA
<213> ORGANISM: Cauliflower mosaic virus

<400> SEQUENCE: 8
caccattaat taagtcaaag attcaaatag aggacctaac                             40

<210> SEQ ID NO 9
<211> LENGTH: 42
<212> TYPE: DNA
<213> ORGANISM: Cauliflower mosaic virus

<400> SEQUENCE: 9
caccacggac cgtactagtc gtgttctctc caaatgaaat ga                          42

<210> SEQ ID NO 10
<211> LENGTH: 39
<212> TYPE: DNA
<213> ORGANISM: Cochliobolus heterostrophus

<400> SEQUENCE: 10
caccaactag tatgctgtgg cttgcacaag cattgttgg                              39

<210> SEQ ID NO 11
<211> LENGTH: 42
<212> TYPE: DNA
<213> ORGANISM: Cochliobolus heterostrophus

<400> SEQUENCE: 11
caccaggccg gccttatcta aagctgctag tgtccagtgg gg                          42

<210> SEQ ID NO 12
<211> LENGTH: 38
<212> TYPE: DNA
<213> ORGANISM: Commelina yellow mottle virus

<400> SEQUENCE: 12
caccattaat taagtgcaac cactcagaca aaagatgg                               38

<210> SEQ ID NO 13
<211> LENGTH: 48
<212> TYPE: DNA
<213> ORGANISM: Commelina yellow mottle virus

<400> SEQUENCE: 13
caccacggac cgtactagtt agaaccaatt actacactca aagtattc                    48

<210> SEQ ID NO 14
<211> LENGTH: 21
<212> TYPE: DNA
<213> ORGANISM: Trichoderma reesei

<400> SEQUENCE: 14
actttgcgtc ccttgtgacg g                                                 21

<210> SEQ ID NO 15
<211> LENGTH: 21
<212> TYPE: DNA
<213> ORGANISM: Trichoderma reesei
```

```
<400> SEQUENCE: 15
ttgcattggt acagctgcag g                                              21

<210> SEQ ID NO 16
<211> LENGTH: 21
<212> TYPE: DNA
<213> ORGANISM: Trichoderma reesei

<400> SEQUENCE: 16
gactcacgca agctcaattc g                                              21

<210> SEQ ID NO 17
<211> LENGTH: 23
<212> TYPE: DNA
<213> ORGANISM: Trichoderma reesei

<400> SEQUENCE: 17
ccagactctc ctgcgtcacc aat                                            23

<210> SEQ ID NO 18
<211> LENGTH: 24
<212> TYPE: DNA
<213> ORGANISM: Trichoderma reesei

<400> SEQUENCE: 18
ctacaatcat caccacgatg ctcc                                           24

<210> SEQ ID NO 19
<211> LENGTH: 24
<212> TYPE: DNA
<213> ORGANISM: Trichoderma reesei

<400> SEQUENCE: 19
cgacattctc tcctaatcac cagc                                           24

<210> SEQ ID NO 20
<211> LENGTH: 24
<212> TYPE: DNA
<213> ORGANISM: Trichoderma reesei

<400> SEQUENCE: 20
gccgtgccta cctgctttag tatt                                           24

<210> SEQ ID NO 21
<211> LENGTH: 23
<212> TYPE: DNA
<213> ORGANISM: Trichoderma reesei

<400> SEQUENCE: 21
ccactatctc aggtaaccag tac                                            23

<210> SEQ ID NO 22
<211> LENGTH: 24
<212> TYPE: DNA
<213> ORGANISM: Trichoderma reesei

<400> SEQUENCE: 22
gtctcgctcc acttgatgtt ggca                                           24

<210> SEQ ID NO 23
<211> LENGTH: 41
<212> TYPE: DNA
<213> ORGANISM: Cauliflower mosaic virus
```

```
<400> SEQUENCE: 23
caccattaat taagtcaaag attcaaatag aggacctaac a                         41

<210> SEQ ID NO 24
<211> LENGTH: 55
<212> TYPE: DNA
<213> ORGANISM: Cauliflower mosaic virus

<400> SEQUENCE: 24
tgtagagaga gattggtgat ttcagcggta ccgtgttctc tccaaatgaa atgaa         55

<210> SEQ ID NO 25
<211> LENGTH: 59
<212> TYPE: DNA
<213> ORGANISM: Cauliflower mosaic virus

<400> SEQUENCE: 25
caccaactag tgagaaatag agagagatag atttgtagag agagattggt gatttcagc     59

<210> SEQ ID NO 26
<211> LENGTH: 42
<212> TYPE: DNA
<213> ORGANISM: Unknown
<220> FEATURE:
<223> OTHER INFORMATION: CaMV/T.reesei

<400> SEQUENCE: 26
agagggagag agggaggagg cgtgttctct ccaaatgaaa tg                       42

<210> SEQ ID NO 27
<211> LENGTH: 42
<212> TYPE: DNA
<213> ORGANISM: Unknown
<220> FEATURE:
<223> OTHER INFORMATION: CaMV/T.reesei

<400> SEQUENCE: 27
gagagtctgg cggggtagct cgtgttctct ccaaatgaaa tg                       42

<210> SEQ ID NO 28
<211> LENGTH: 42
<212> TYPE: DNA
<213> ORGANISM: Unknown
<220> FEATURE:
<223> OTHER INFORMATION: CaMV/T.reesei

<400> SEQUENCE: 28
gcgaacagaa gccgcatcgt cgtgttctct ccaaatgaaa tg                       42

<210> SEQ ID NO 29
<211> LENGTH: 42
<212> TYPE: DNA
<213> ORGANISM: Unknown
<220> FEATURE:
<223> OTHER INFORMATION: CaMV/T.reesei

<400> SEQUENCE: 29
catttcattt ggagagaaca cgcctcctcc ctctctccct ct                       42

<210> SEQ ID NO 30
<211> LENGTH: 42
<212> TYPE: DNA
<213> ORGANISM: Unknown
<220> FEATURE:
```

<223> OTHER INFORMATION: CaMV/T.reesei

<400> SEQUENCE: 30
catttcattt ggagagaaca cgagctaccc cgccagactc tc        42

<210> SEQ ID NO 31
<211> LENGTH: 42
<212> TYPE: DNA
<213> ORGANISM: Unknown
<220> FEATURE:
<223> OTHER INFORMATION: CaMV/T.reesei

<400> SEQUENCE: 31
catttcattt ggagagaaca cgacgatgcg gcttctgttc gc        42

<210> SEQ ID NO 32
<211> LENGTH: 39
<212> TYPE: DNA
<213> ORGANISM: Trichoderma reesei

<400> SEQUENCE: 32
caccaactag ttttgtatct gcgaattgag cttgcgtga            39

<210> SEQ ID NO 33
<211> LENGTH: 2610
<212> TYPE: DNA
<213> ORGANISM: Cochliobolus heterostrophus

<400> SEQUENCE: 33
atgctgtggc ttgcacaagc attgttggtc ggccttgccc aggcatcgcc caggttccct 60
cgtgctacca acgacaccgg cagtgattct ttgaacaatg cccagagccc gccattctac 120
ccaagtcctt gggtagatcc caccaccaag gactgggcgg ctgcctatga aaaagcaaag 180
gcttttgtta gccaattgac tcttattgag aaggtcaacc tcaccaccgg cactggatgg 240
cagagcgacc actgcgttgg taacgtgggc gctattcctc gccttggctt tgatcccctc 300
tgcctccagg acagccctct cggcatccgt ttcgcagact acgtttctgc tttcccagca 360
ggtggcacca ttgctgcatc atgggaccgc tatgagtttt acacccgcgg taacgagatg 420
ggtaaggagc accgaaggaa gggagtcgac gttcagcttg gtcctgccat tggacctctt 480
ggtcgccacc ccaagggcgg tcgtaactgg gaaggcttca gtcctgatcc tgtactttcc 540
ggtgtggccg tgagcgaaac agtccgcggt atccaggatg ctggtgtcat tgcctgcact 600
aagcacttcc ttctgaacga gcaagaacat ttccgtcagc ccggcagttt cggagatatc 660
ccctttgtcg atgccatcag ctccaatacc gatgacacga ctctacacga gctctacctg 720
tggccctttg ccgacgccgt ccgcgctggt actggtgcca tcatgtgctc ttacaacaag 780
gccaacaact cgcaactctg ccaaaactcg caccttcaaa actatattct caagggcgag 840
cttggcttcc agggtttcat tgtatctgac tgggatgcac agcactcggg cgttgcgtcg 900
gcttatgctg gattggacat gactatgcct ggtgatactg gattcaacac tggactgtcc 960
ttctggggcg ctaacatgac cgtctccatt ctcaacggca ccattcccca gtggcgtctc 1020
gacgatgcgg ccatccgtat catgaccgca tactactttg tcggccttga tgagtctatc 1080
cctgtcaact ttgacagctg gcaaactagc acgtacggat tcgagcattt tttcggaaag 1140
aagggcttcg gtctgatcaa caagcacatt gacgttcgcg aggagcactt ccgctccatc 1200
cgccgctctg ctgccaagtc aaccgttctc ctcaagaact ctggcgtcct tcccctctct 1260
ggaaaggaga agtggactgc tgtatttgga gaagatgctg gcgaaaaccc gctgggcccc 1320

```
aacggatgcg ctgaccgcgg ctgcgactct ggcaccttgg ccatgggctg gggttcggga    1380
actgcagact tcccttacct cgtcactcct ctcgaagcca tcaagcgtga ggttggcgag    1440
aatggcggcg tgatcacttc ggtcacagac aactacgcca cttcgcagat ccagaccatg    1500
gccagcaggg ccagccactc gattgtcttc gtcaatgccg actctggtga aggttacatc    1560
actgttgata caacatgggt tgaccgcaac aacatgactg tgtggggcaa tggtgatgtg    1620
cttgtcaaga atatctctgc tctgtgcaac aacacgattg tggttatcca ctctgtcggc    1680
ccagtcatta ttgacgcctg gaaggccaac gacaacgtga ctgccattct ctgggctggt    1740
cttcctggcc aggagtctgg taactcgatt gctgacattc tatacggaca ccacaaccct    1800
ggtggcaagc tccccttcac cattggcagc tcttcagagg agtatggccc tgatgtcatc    1860
tacgagccca cgaacggcat cctcagccct caggccaact ttgaagaggg cgtcttcatt    1920
gactaccgcg cgtttgacaa ggcgggcatt gagcccacgt acgaatttgg ctttggtctt    1980
tcgtacacga cttttgaata ctcggacctc aaggtcactg cgcagtctgc cgaggcttac    2040
aagcctttca ccggccagac ttcggctgcc cctacattcg gaaacttcag caagaacccc    2100
gaggactacc agtaccctcc cggccttgtt taccccgaca cgttcatcta cccctacctc    2160
aactcgactg acctcaagac ggcatctcag gatcccgagt acggcctcaa cgttacctgg    2220
cccaagggct ctaccgatgg ctcgcctcag accccgcattg cggctggtgg tgcgcccggc    2280
ggtaaccccc agctctggga cgttttgttc aaggtcgagg ccacgatcac caacactggt    2340
cacgttgctg gtgacgaggt ggcccaggcg tacatctcgc ttggtggccc caacgacccc    2400
aaggtgctac tccgtgactt tgaccgcttg accatcaagc ctggtgagag cgctgttttc    2460
acagccaaca tcacccgccg tgatgtcagc aactgggaca ctgtcagcca gaactgggtc    2520
attaccgagt accccaagac gatccacgtt ggtgccagtt cgaggaacct tcctctttct    2580
gccccactgg acactagcag ctttagataa                                     2610
```

<210> SEQ ID NO 34
<211> LENGTH: 868
<212> TYPE: PRT
<213> ORGANISM: Cochliobolus heterostrophus

<400> SEQUENCE: 34

```
Met Leu Trp Leu Ala Gln Ala Leu Leu Val Gly Leu Ala Gln Ala Ser
1               5                   10                  15

Pro Arg Phe Pro Arg Ala Thr Asn Asp Thr Gly Ser Asp Ser Leu Asn
            20                  25                  30

Asn Ala Gln Ser Pro Pro Phe Tyr Pro Ser Pro Trp Val Asp Pro Thr
        35                  40                  45

Thr Lys Asp Trp Ala Ala Tyr Glu Lys Ala Lys Ala Phe Val Ser
    50                  55                  60

Gln Leu Thr Leu Ile Glu Lys Val Asn Leu Thr Thr Gly Thr Gly Trp
65                  70                  75                  80

Gln Ser Asp His Cys Val Gly Asn Val Gly Ala Ile Pro Arg Leu Gly
                85                  90                  95

Phe Asp Pro Leu Cys Leu Gln Asp Ser Pro Leu Gly Ile Arg Phe Ala
            100                 105                 110

Asp Tyr Val Ser Ala Phe Pro Ala Gly Gly Thr Ile Ala Ala Ser Trp
        115                 120                 125

Asp Arg Tyr Glu Phe Tyr Thr Arg Gly Asn Glu Met Gly Lys Glu His
    130                 135                 140
```

```
Arg Arg Lys Gly Val Asp Val Gln Leu Gly Pro Ala Ile Gly Pro Leu
145                 150                 155                 160

Gly Arg His Pro Lys Gly Gly Arg Asn Trp Glu Gly Phe Ser Pro Asp
                165                 170                 175

Pro Val Leu Ser Gly Val Ala Val Ser Glu Thr Val Arg Gly Ile Gln
            180                 185                 190

Asp Ala Gly Val Ile Ala Cys Thr Lys His Phe Leu Leu Asn Glu Gln
        195                 200                 205

Glu His Phe Arg Gln Pro Gly Ser Phe Gly Asp Ile Pro Phe Val Asp
    210                 215                 220

Ala Ile Ser Ser Asn Thr Asp Thr Thr Leu His Glu Leu Tyr Leu
225                 230                 235                 240

Trp Pro Phe Ala Asp Ala Val Arg Ala Gly Thr Gly Ala Ile Met Cys
                245                 250                 255

Ser Tyr Asn Lys Ala Asn Asn Ser Gln Leu Cys Gln Asn Ser His Leu
            260                 265                 270

Gln Asn Tyr Ile Leu Lys Gly Glu Leu Gly Phe Gln Gly Phe Ile Val
        275                 280                 285

Ser Asp Trp Asp Ala Gln His Ser Gly Val Ala Ser Ala Tyr Ala Gly
290                 295                 300

Leu Asp Met Thr Met Pro Gly Asp Thr Gly Phe Asn Thr Gly Leu Ser
305                 310                 315                 320

Phe Trp Gly Ala Asn Met Thr Val Ser Ile Leu Asn Gly Thr Ile Pro
                325                 330                 335

Gln Trp Arg Leu Asp Asp Ala Ala Ile Arg Ile Met Thr Ala Tyr Tyr
            340                 345                 350

Phe Val Gly Leu Asp Glu Ser Ile Pro Val Asn Phe Asp Ser Trp Gln
        355                 360                 365

Thr Ser Thr Tyr Gly Phe Glu His Phe Phe Gly Lys Lys Gly Phe Gly
    370                 375                 380

Leu Ile Asn Lys His Ile Asp Val Arg Glu Glu His Phe Arg Ser Ile
385                 390                 395                 400

Arg Arg Ser Ala Ala Lys Ser Thr Val Leu Leu Lys Asn Ser Gly Val
                405                 410                 415

Leu Pro Leu Ser Gly Lys Glu Lys Trp Thr Ala Val Phe Gly Glu Asp
            420                 425                 430

Ala Gly Glu Asn Pro Leu Gly Pro Asn Gly Cys Ala Asp Arg Gly Cys
        435                 440                 445

Asp Ser Gly Thr Leu Ala Met Gly Trp Gly Ser Gly Thr Ala Asp Phe
    450                 455                 460

Pro Tyr Leu Val Thr Pro Leu Glu Ala Ile Lys Arg Glu Val Gly Glu
465                 470                 475                 480

Asn Gly Gly Val Ile Thr Ser Val Thr Asp Asn Tyr Ala Thr Ser Gln
                485                 490                 495

Ile Gln Thr Met Ala Ser Arg Ala Ser His Ser Ile Val Phe Val Asn
            500                 505                 510

Ala Asp Ser Gly Glu Gly Tyr Ile Thr Val Asp Asn Asn Met Gly Asp
        515                 520                 525

Arg Asn Asn Met Thr Val Trp Gly Asn Gly Asp Val Leu Val Lys Asn
    530                 535                 540

Ile Ser Ala Leu Cys Asn Asn Thr Ile Val Val Ile His Ser Val Gly
545                 550                 555                 560
```

-continued

```
Pro Val Ile Ile Asp Ala Trp Lys Ala Asn Asp Val Thr Ala Ile
            565                 570                 575

Leu Trp Ala Gly Leu Pro Gly Gln Glu Ser Gly Asn Ser Ile Ala Asp
            580                 585                 590

Ile Leu Tyr Gly His His Asn Pro Gly Gly Lys Leu Pro Phe Thr Ile
            595                 600                 605

Gly Ser Ser Ser Glu Glu Tyr Gly Pro Asp Val Ile Tyr Glu Pro Thr
            610                 615                 620

Asn Gly Ile Leu Ser Pro Gln Ala Asn Phe Glu Gly Val Phe Ile
625                 630                 635                 640

Asp Tyr Arg Ala Phe Asp Lys Ala Gly Ile Glu Pro Thr Tyr Glu Phe
                645                 650                 655

Gly Phe Gly Leu Ser Tyr Thr Thr Phe Glu Tyr Ser Asp Leu Lys Val
                660                 665                 670

Thr Ala Gln Ser Ala Glu Ala Tyr Lys Pro Phe Thr Gly Gln Thr Ser
            675                 680                 685

Ala Ala Pro Thr Phe Gly Asn Phe Ser Lys Asn Pro Glu Asp Tyr Gln
            690                 695                 700

Tyr Pro Pro Gly Leu Val Tyr Pro Asp Thr Phe Ile Tyr Pro Tyr Leu
705                 710                 715                 720

Asn Ser Thr Asp Leu Lys Thr Ala Ser Gln Asp Pro Glu Tyr Gly Leu
                725                 730                 735

Asn Val Thr Trp Pro Lys Gly Ser Thr Asp Gly Ser Pro Gln Thr Arg
            740                 745                 750

Ile Ala Ala Gly Gly Ala Pro Gly Asn Pro Gln Leu Trp Asp Val Leu
            755                 760                 765

Phe Lys Val Glu Ala Thr Ile Thr Asn Thr Gly His Val Ala Gly Asp
    770                 775                 780

Glu Val Ala Gln Ala Tyr Ile Ser Leu Gly Gly Pro Asn Asp Pro Lys
785                 790                 795                 800

Val Leu Leu Arg Asp Phe Asp Arg Leu Thr Ile Lys Pro Gly Glu Ser
                805                 810                 815

Ala Val Phe Thr Ala Asn Ile Thr Arg Arg Asp Val Ser Asn Trp Asp
            820                 825                 830

Thr Val Ser Gln Asn Trp Val Ile Thr Glu Tyr Pro Lys Thr Ile His
            835                 840                 845

Val Gly Ala Ser Ser Arg Asn Leu Pro Leu Ser Ala Pro Leu Asp Thr
850                 855                 860

Ser Ser Phe Arg
865
```

USE OF PLANT PROMOTERS IN FILAMENTOUS FUNGI

1. BACKGROUND

Figure 1:
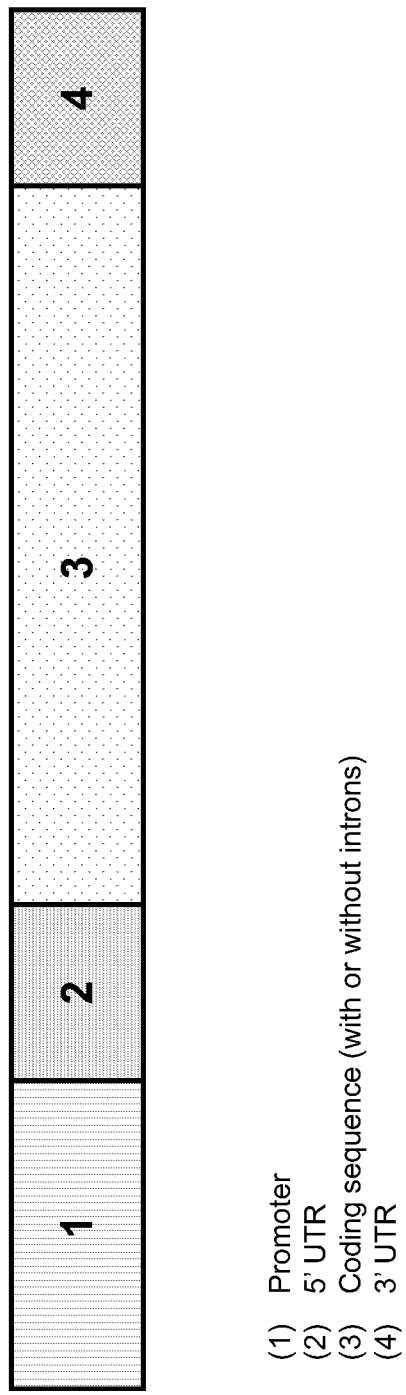

The use of recombinant expression has greatly simplified the production of large quantities of commercially valuable proteins. Currently, there is a varied selection of expression systems from which to choose for the production of any given protein, including prokaryotic and eukaryotic hosts. A variety of gene expression systems have been developed for use with filamentous fungal cells. Many systems entail the use of inducible promoters, the majority of which require the addition of an exogenous inducer molecule to the culture which is cost prohibitive in large scale commercial fermentations, or endogenous promoters that are susceptible to regulation by endogenous filamentous fungal proteins. Thus, there is a need for expression systems that are economically viable and provide robust expression in large scale commercial fermentations.

2. SUMMARY

The present disclosure relates to the use of heterologous promoters to drive recombinant polypeptide expression in filamentous fungi. More particularly, the present disclosure relates to the use of promoters that are operable in plant cells to drive recombinant polypeptide expression in filamentous fungi. The present disclosure is based, in part, on Applicants' discovery that promoters that are constitutively active in plant cells are capable of eliciting high expression levels in filamentous fungi such as *Trichoderma reesei*, particularly when the 5' UTR sequence normally associated with the promoter is replaced by a filamentous fungal 5' UTR sequence. Thus, the present disclosure relates to recombinant filamentous fungal expression systems utilizing promoters operable in plant cells, which are preferably constitutive promoters. Such promoters can be derived from a plant genome or the genome of a plant virus, and are collectively referred to herein as "plant promoters."

Thus, the present disclosure provides expression cassettes comprising a plant promoter operably linked to a coding sequence for a polypeptide of interest (a "POI"). Plant promoters that are suitable for recombinant expression in filamentous fungi include, but are not limited to, the cauliflower mosaic virus (CaMV) 35S promoter or the *Commelina* yellow mottle virus (CoYMV) promoter. Additional promoters suitable for practicing the present invention are described in Section 4.1.1.

The sequence encoding the POI can be from a prokaryotic (e.g., bacterial), eukaryotic (e.g., plant, filamentous fungal, yeast or mammalian) or viral source. It can optionally include introns. In some embodiments, the polypeptide coding sequence comprises a signal sequence, which directs the POI to be secreted by the filamentous fungal cell. In a specific exemplary embodiment, the polypeptide coding sequence is a polypeptide coding sequence of a *Cochliobolus heterostrophus* β-glucosidase gene. Further POIs are described in Section 4.1.3.

In order to achieve robust expression of the POI from the mRNA transcript, the expression cassette preferably includes a sequence that corresponds to a 5' untranslated region (5' UTR) in the mRNA resulting from transcription of the expression cassette (for convenience referred to as a "5' UTR" in the expression cassette). A 5' UTR can contain elements controlling gene expression by way of regulatory elements. It begins at the transcription start site and ends one nucleotide (nt) before the start codon of the coding region. A 5' UTR that is operable in a filamentous fungal cell can be included in the expression cassettes of the disclosure. The source of the 5' UTR can vary provided it is operable in the filamentous fungal cell. In various embodiments, the 5' UTR can be derived from a yeast gene or a filamentous fungal gene. The 5' UTR can be from the same species one other component in the expression cassette (e.g., the promoter or the polypeptide coding sequence), or from a different species than the other component. The 5' UTR can be from the same species as the filamentous fungal cell that the expression construct is intended to operate in. By of example and not limitation, the 5' UTR can from a *Trichoderma* species, such as *Trichoderma reesei*. In an exemplary embodiment, the 5' UTR comprises a sequence corresponding to a fragment of a 5' UTR from a *T. reesei* glyceraldehyde-3-phosphate dehydrogenase (gpd). In another specific embodiment, the 5' UTR comprises a sequence corresponding to a CaMV S1 5' UTR. Additional 5' UTRs are described in Section 4.1.2.

For effective processing of the transcript encoding the POI, the expression cassette further includes a sequence that corresponds to a 3' untranslated region (3' UTR) in the mRNA resulting from transcription of the expression cassette (for convenience referred to as a "3' UTR" in the expression cassette). A 3' UTR minimally includes a polyadenylation signal, which directs cleavage of the transcript followed by the addition of a poly(A) tail that is important for the nuclear export, translation, and stability of mRNA. As with the 5' UTR, the 3' UTR can be derived from a yeast gene or a filamentous fungal gene. Additional 3' UTRs are described in Section 4.1.4.

Accordingly, in certain aspects, as illustrated in FIG. 1, the present disclosure provides expression cassettes comprising, operably linked to 5' and to 3' direction: (1) a plant promoter, (2) a 5' UTR (i.e., a sequence coding for a 5' UTR), (3) a coding sequence for a POI, and (4) a 3' UTR (i.e., a coding sequence for a 3' UTR). Each of these components is described below and in the corresponding sub-section of Section 4.1.

The expression cassettes of the disclosure can encode more than one POI (e.g., a first POI, a second POI, and optionally a third or more POIs). In embodiments where the expression cassette comprises more than one polypeptide coding sequence, the expression cassette can include an internal ribosome binding entry site ("IRES") sequence between the POI coding sequences.

The present disclosure further provides filamentous fungal cells engineered to contain an expression cassette. Recombinant filamentous fungal cells may be from any species of filamentous fungus. In some embodiments, the filamentous fungal cell is a *Trichoderma* sp., e.g. *Trichoderma reesei*. The expression cassette can be extra-genomic or part of the filamentous fungal cell genome. One, several, or all components in an expression cassette can be introduced into a filamentous fungal cell by one or more vectors. Accordingly, the present disclosure also provides vectors comprising expression cassettes or components thereof (e.g., a promoter). The vectors can also include targeting sequences that are capable of directing integration of the expression cassette or expression cassette component into a filamentous cell by homologous recombination. For example, the vector can include a plant promoter flanked by sequences corresponding to a filamentous fungal gene encoding a POI such that upon transformation of the vector into a filamentous fungal cell the flanking sequences will direct integration of the promoter sequence into a location of the filamentous fungal genome where it is operably linked to the POI coding sequence and directs recombinant expression of the POI.

The present disclosure further provides vectors comprising, operably linked in a 5' to 3' direction, a plant promoter, a 5' UTR sequence, one or more unique restriction sites, and a 3' UTR. The unique restriction sites facilitate cloning of any POI coding sequence into the vector to generate an expression cassette of the disclosure.

The vectors are typically capable of autonomous replication in a prokaryotic (e.g., *E. coli*) and/or eukaryotic (e.g., filamentous fungal) cells and thus contain an origin of replication that is operable in such cells. The vectors preferably include a selectable marker, such as an antibiotic resistance marker or an auxotrophy marker, suitable for selection in prokaryotic or eukaryotic cells.

Methods of making the recombinant filamentous fungal cells described herein include methods of introducing vectors comprising expression cassettes or components thereof into filamentous fungal cells and, optionally, selecting for filamentous fungal cells whose genomes contain an expression cassette of the disclosure (for example by integration of an entire expression cassette or a portion thereof). Such methods are described in more detail in Section 4.5 below and in the Examples.

Also provided herein are methods of using the recombinant filamentous fungal cells described herein to produce a POI. Generally, the methods comprise culturing a recombinant filamentous fungal cell comprising an expression cassette of the disclosure under conditions that result in expression of the POI. Optionally, the methods can further include a step of recovering the POI from cell lysates or, where a secreted POI is produced, from the culture medium. The methods can further comprise additional polypeptide purification or isolation steps, as described below in Section 4.6. The recombinant filamentous fungal cells of the disclosure can be used to produce cellulase compositions. Where the production of cellulase compositions (including whole cellulase compositions and fermentation broths) is desired, the recombinant filamentous fungal cells can be engineered to express as POIs one or more cellulases, hemicellulases and/or accessory proteins. Exemplary cellulases, hemicellulases and/or accessory proteins are described in Section 4.1.3. The cellulase compositions can be used, inter alia, in processes for saccharifying biomass. Additional details of saccharification reactions, and additional applications of the variant β-glucosidase polypeptides, are provided in Section 4.6.

All publications, patents, patent applications, GenBank sequences, Accession numbers, and ATCC deposits, cited herein are hereby expressly incorporated by reference for all purposes.

3. BRIEF DESCRIPTION OF THE FIGURES

FIG. 1 provides a schematic drawing of an expression cassette comprising (1) a promoter, (2) a 5' untranslated region (5' UTR), (3) a coding sequence, with or without introns, and (4) a 3' untranslated region (3' UTR).

Figure 2A:
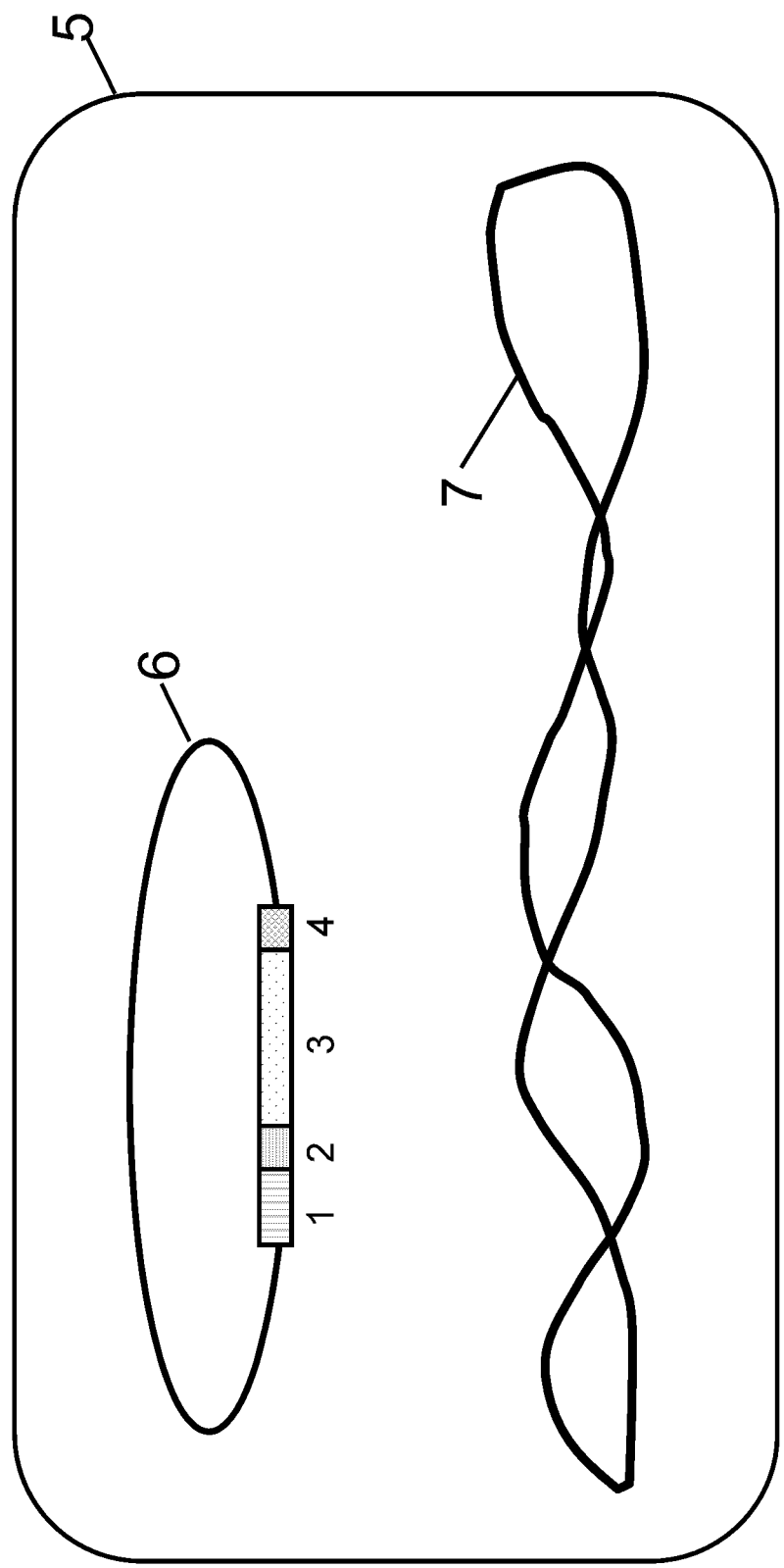
Figure 2B:
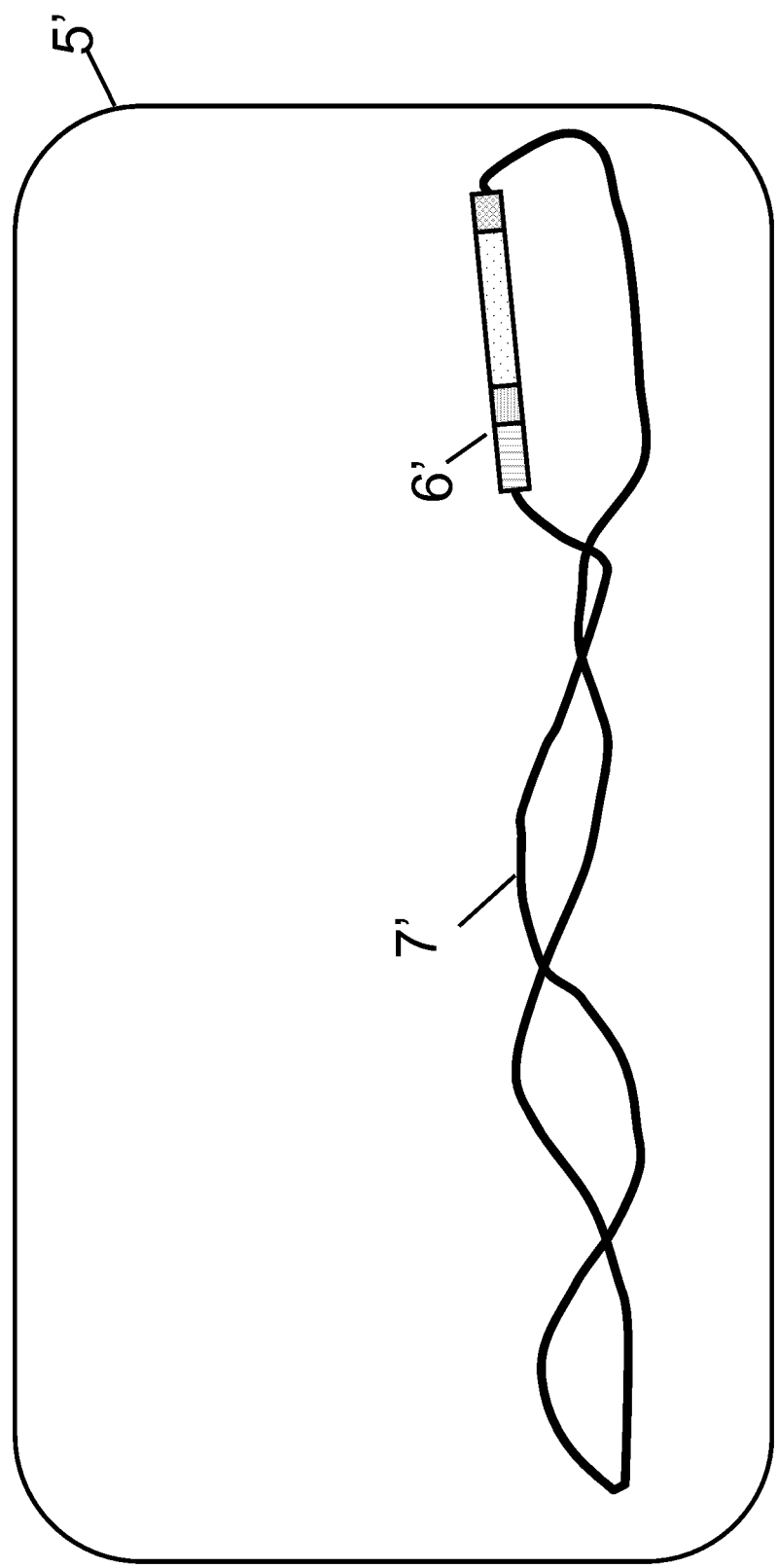
Figure 2C:
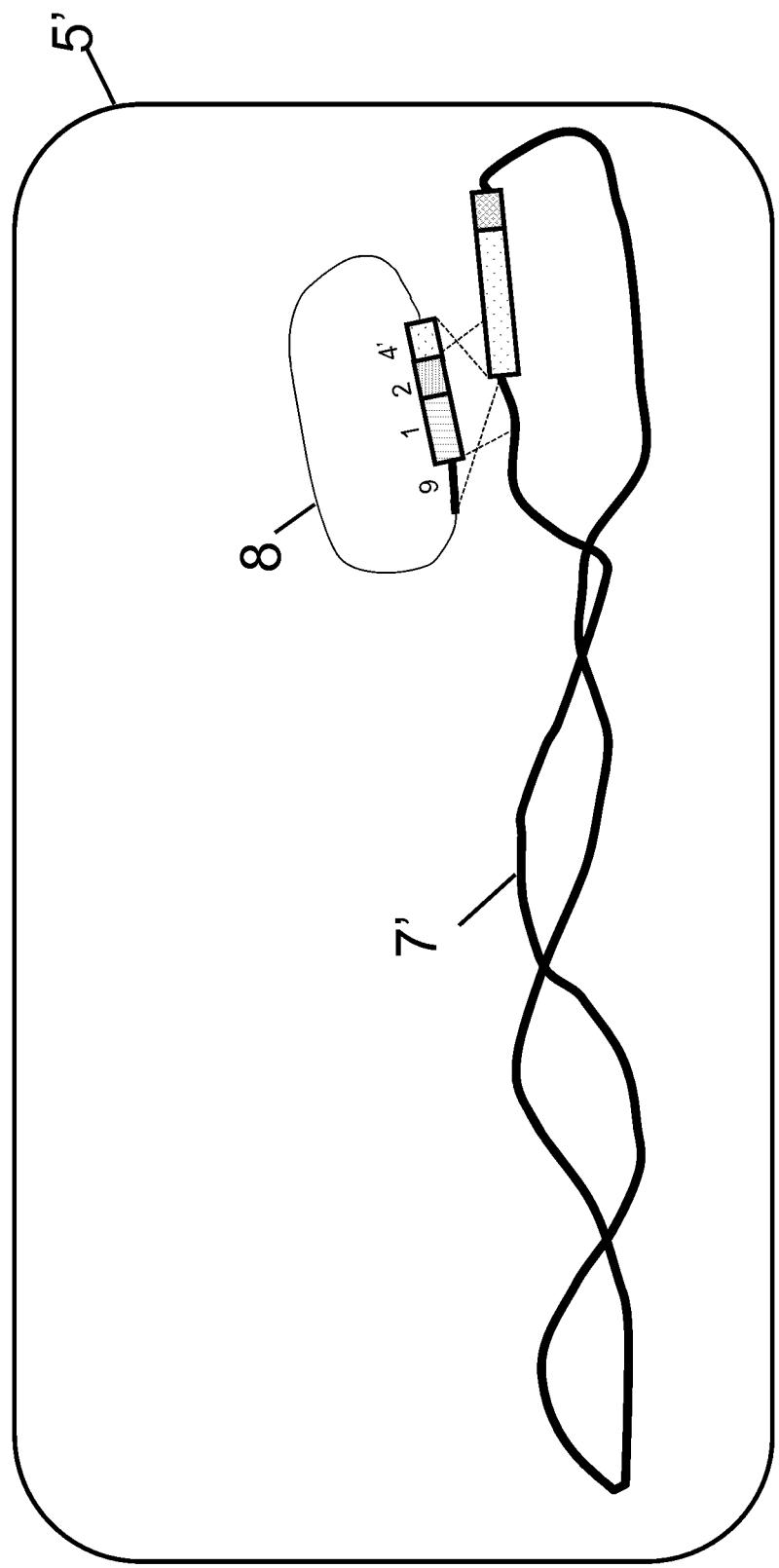

FIGS. 2A-2C provide schematic drawings of an extragenomic expression cassette (FIG. 2A), a genomic expression cassette (FIG. 2B), and integration of expression cassette components into the genome of a filamentous fungal cell to generate a genomic expression cassette (FIG. 2C).

Figure 3A:
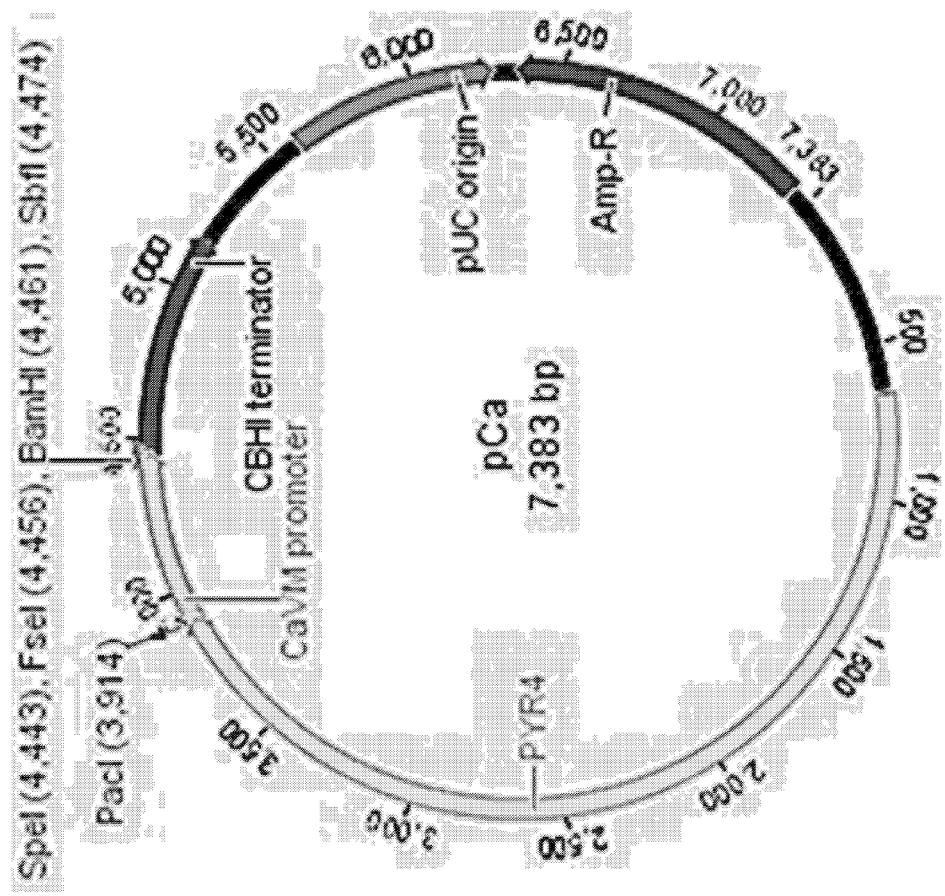
Figure 3B:
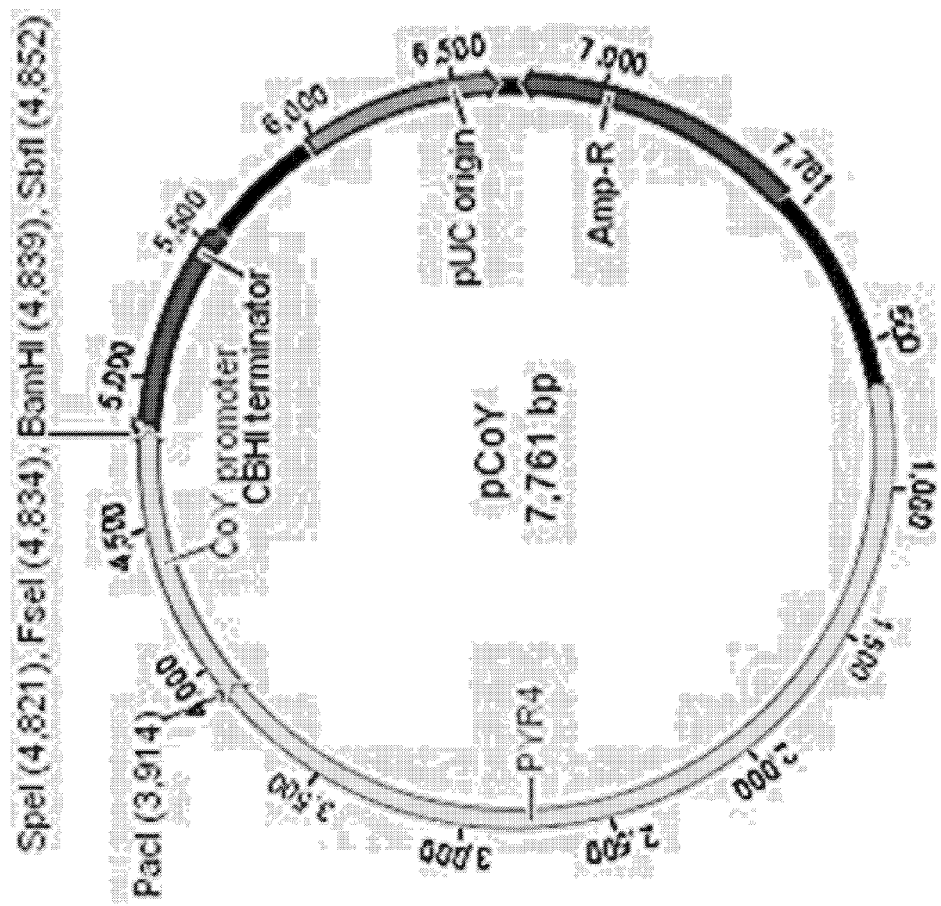

FIG. 3A-3B provides schematic maps of vectors containing plant viral promoters operable in filamentous fungal cells. FIG. 3A illustrates a vector, referred to as pCa, comprising a plant viral promoter from cauliflower mosaic virus (CaMV 35S) and the terminator of *Trichoderma reesei* CBHI gene, which includes a 3' UTR. pCa includes unique restriction sites between the 5' and 3' UTR sequences (SpeI, FseI, BamHI, SbfI), into which the POI coding sequence(s) can be cloned, and a selectable marker gene, pyr4. FIG. 3B illustrates a vector, referred to as pCoY, comprising a plant viral promoter from Commelina yellow mottle virus (CoYMV) and the terminator of *Trichoderma reesei* CBHI gene, which includes a 3' UTR. pCoY includes unique restriction sites between the 5' and 3' UTR sequences (SpeI, FseI, BamHI, SbfI), into which the POI coding sequence(s) can be cloned, and a selectable marker gene, pyr4.

Figure 4:
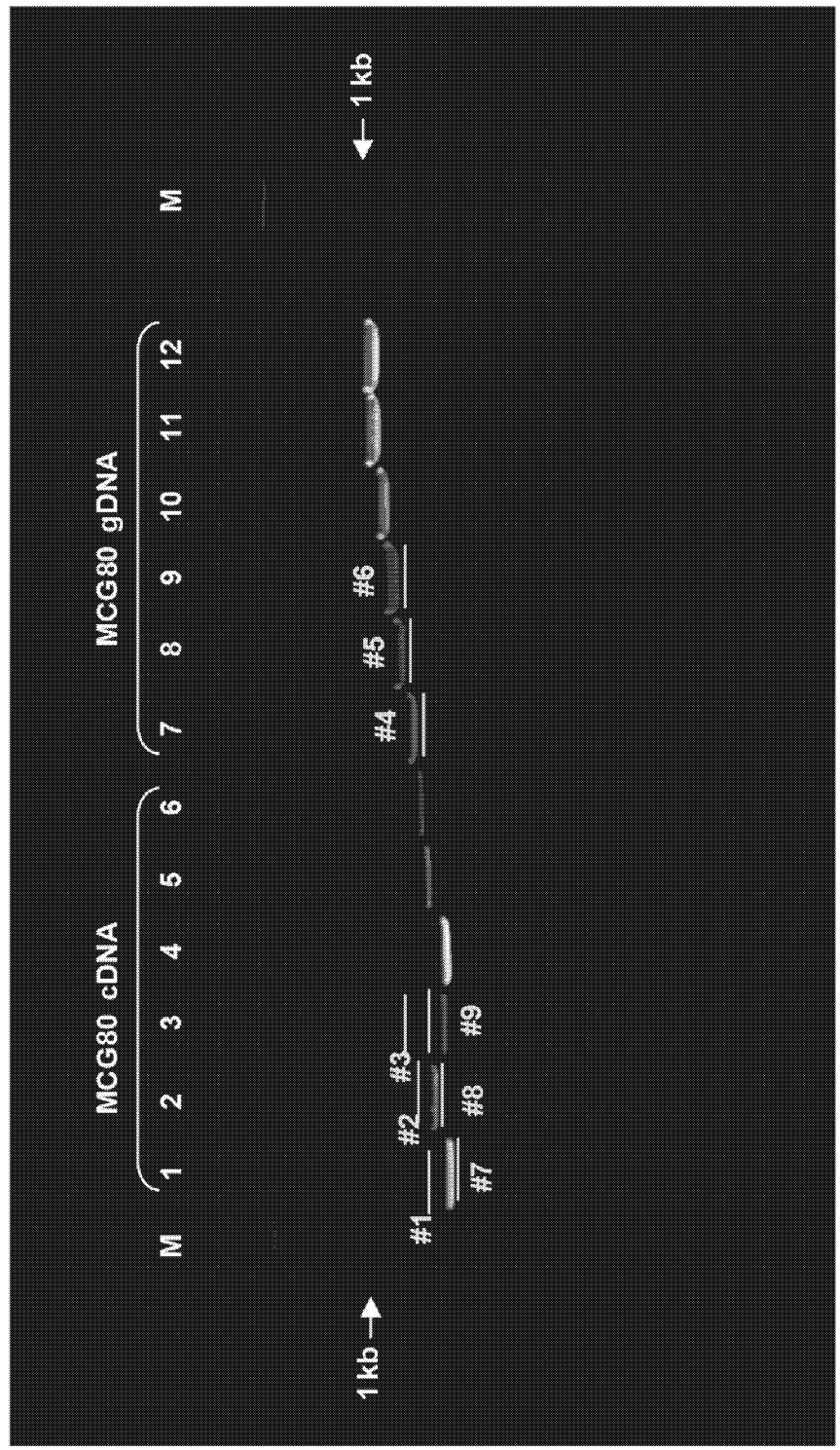

FIG. 4 provides a micrograph mapping the promoter and coding regions for *Trichoderma reesei* glyceraldehyde-3-phosphate dehydrogenase (gpd), showing DNA fragments corresponding to nucleotide sequences in *Trichoderma reesei* glyceraldehyde-3-phosphate dehydrogenase (gpd) cDNA or genomic DNA produced by PCR using nested primers specific to sequences from 34 to 443 bp upstream of the gpd translation start site.

Figure 5A:
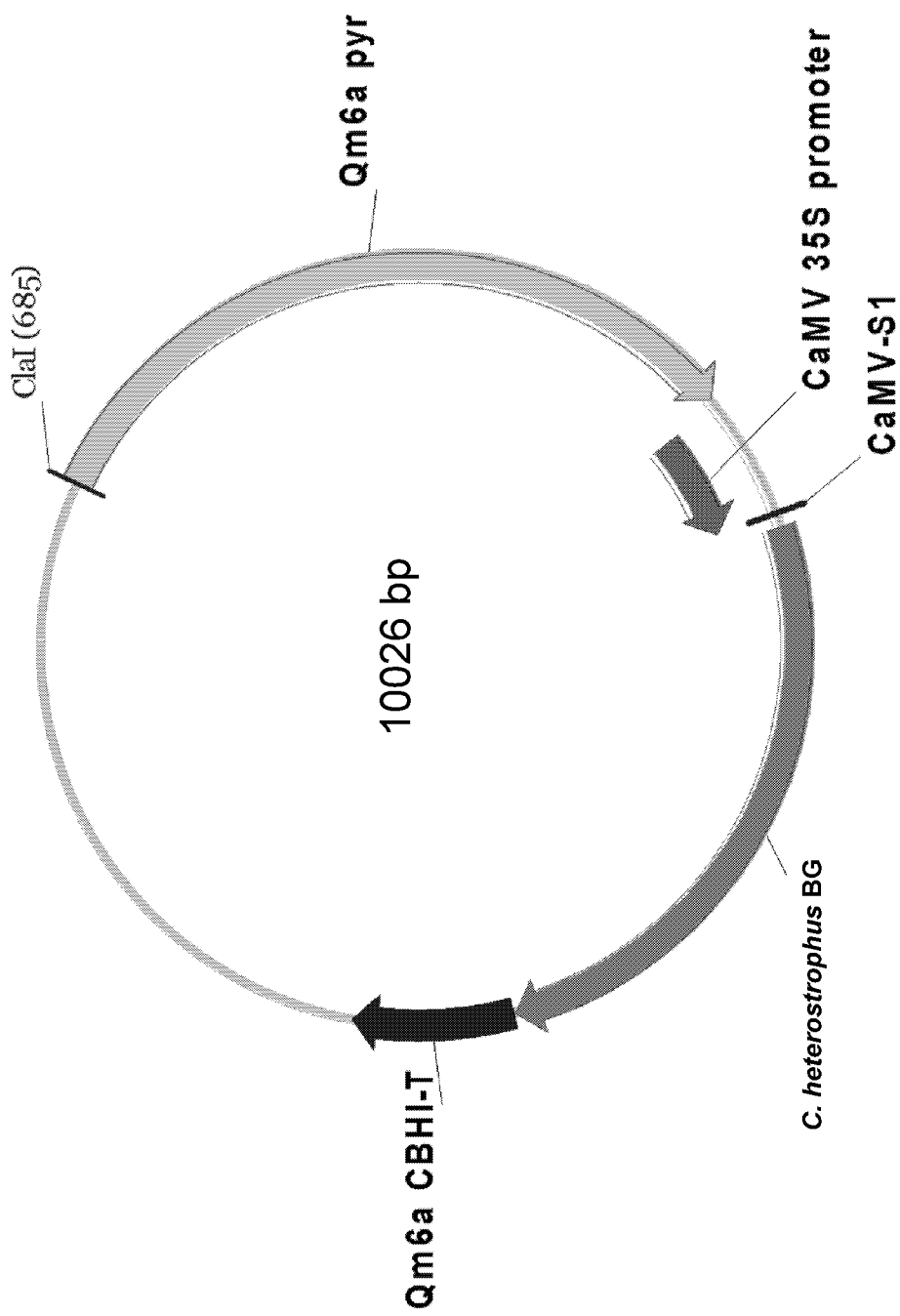
Figure 5B:
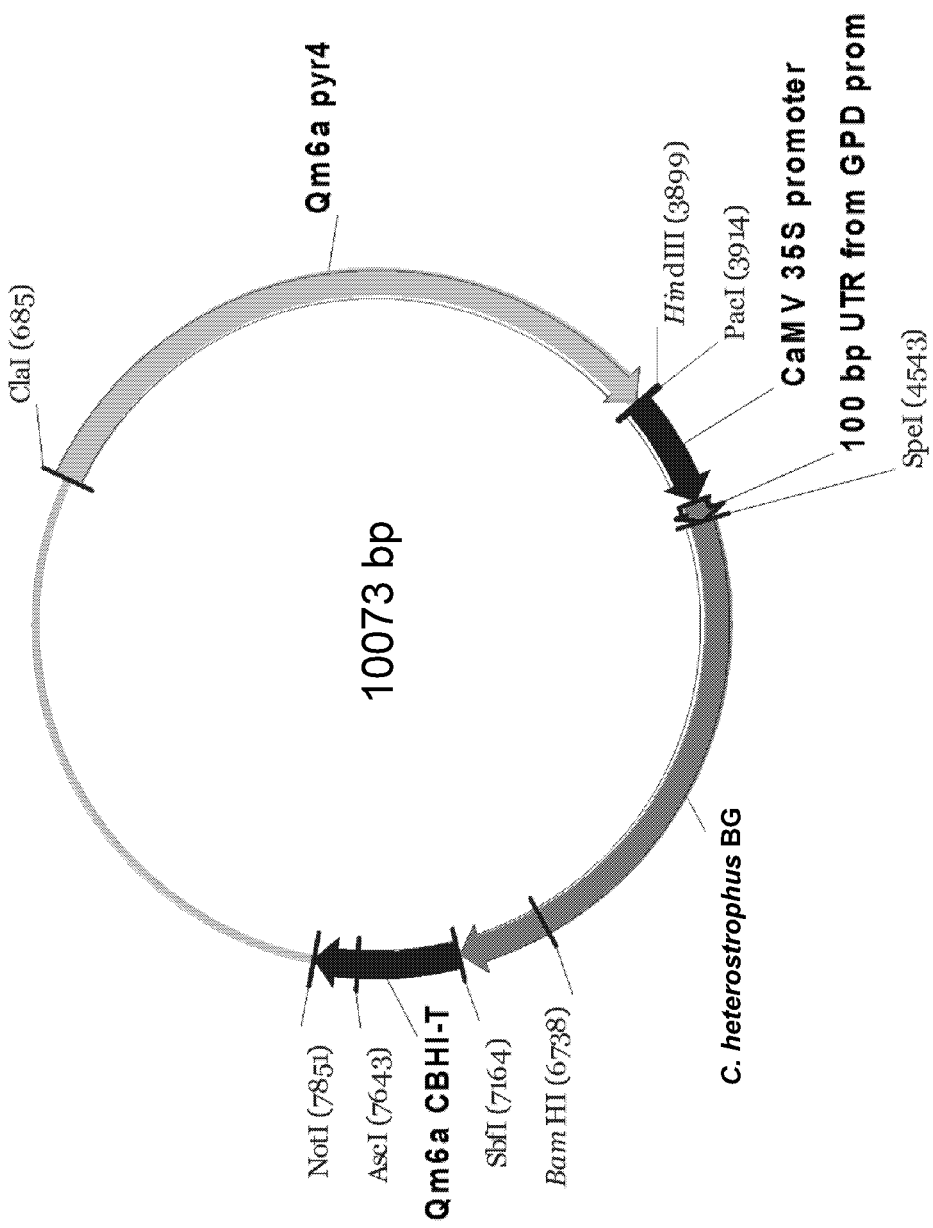
Figure 5C:
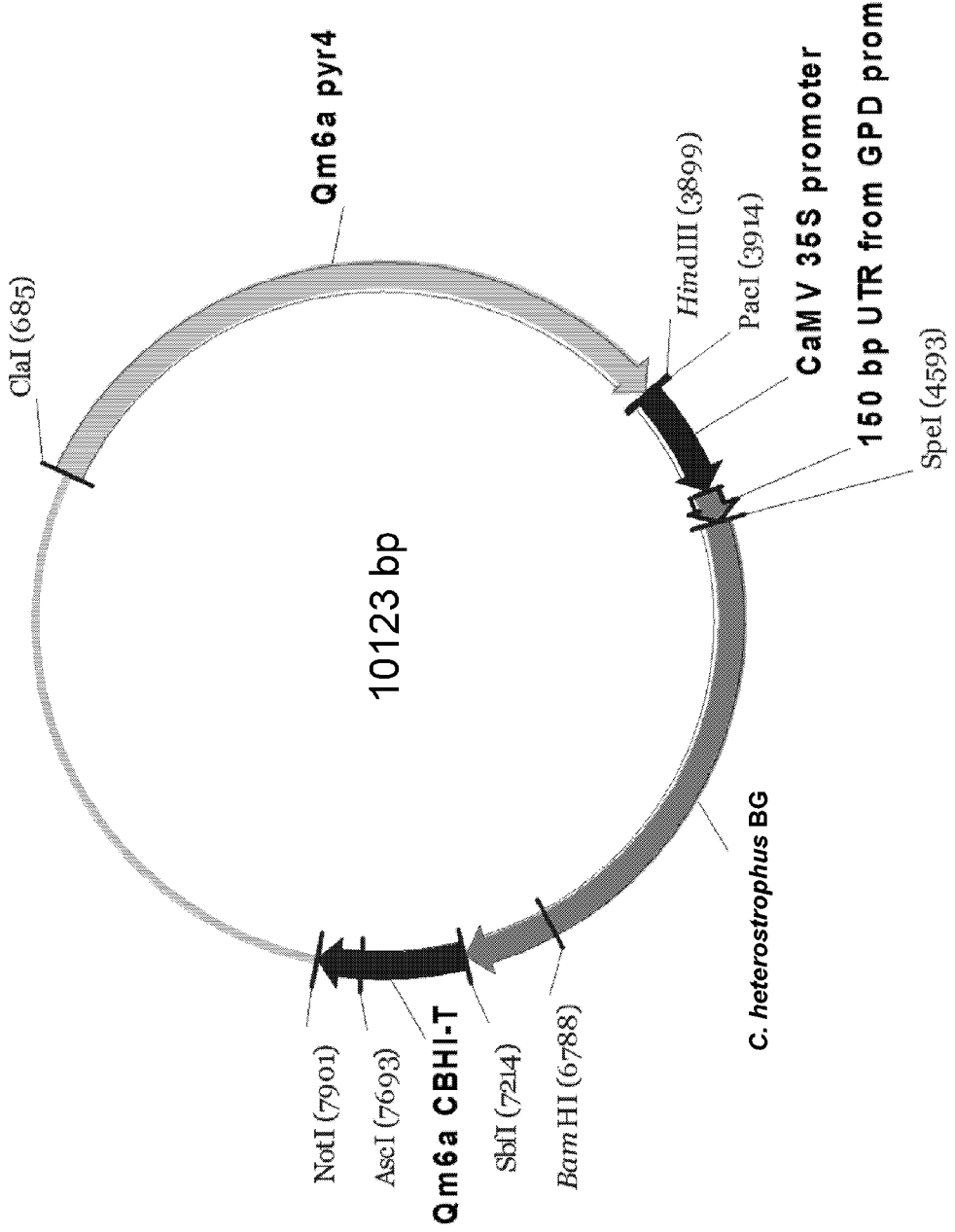
Figure 5D:
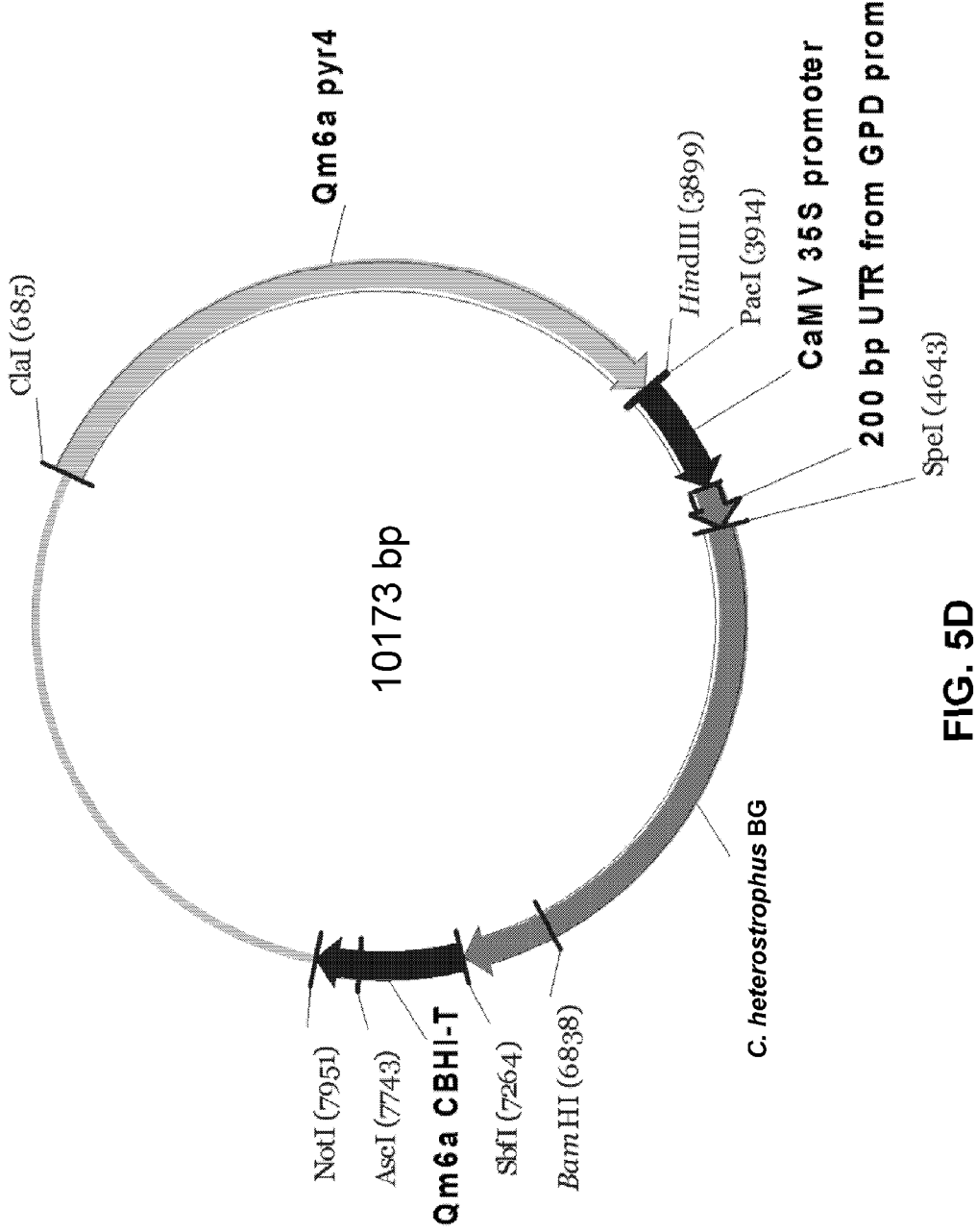
Figure 6A:
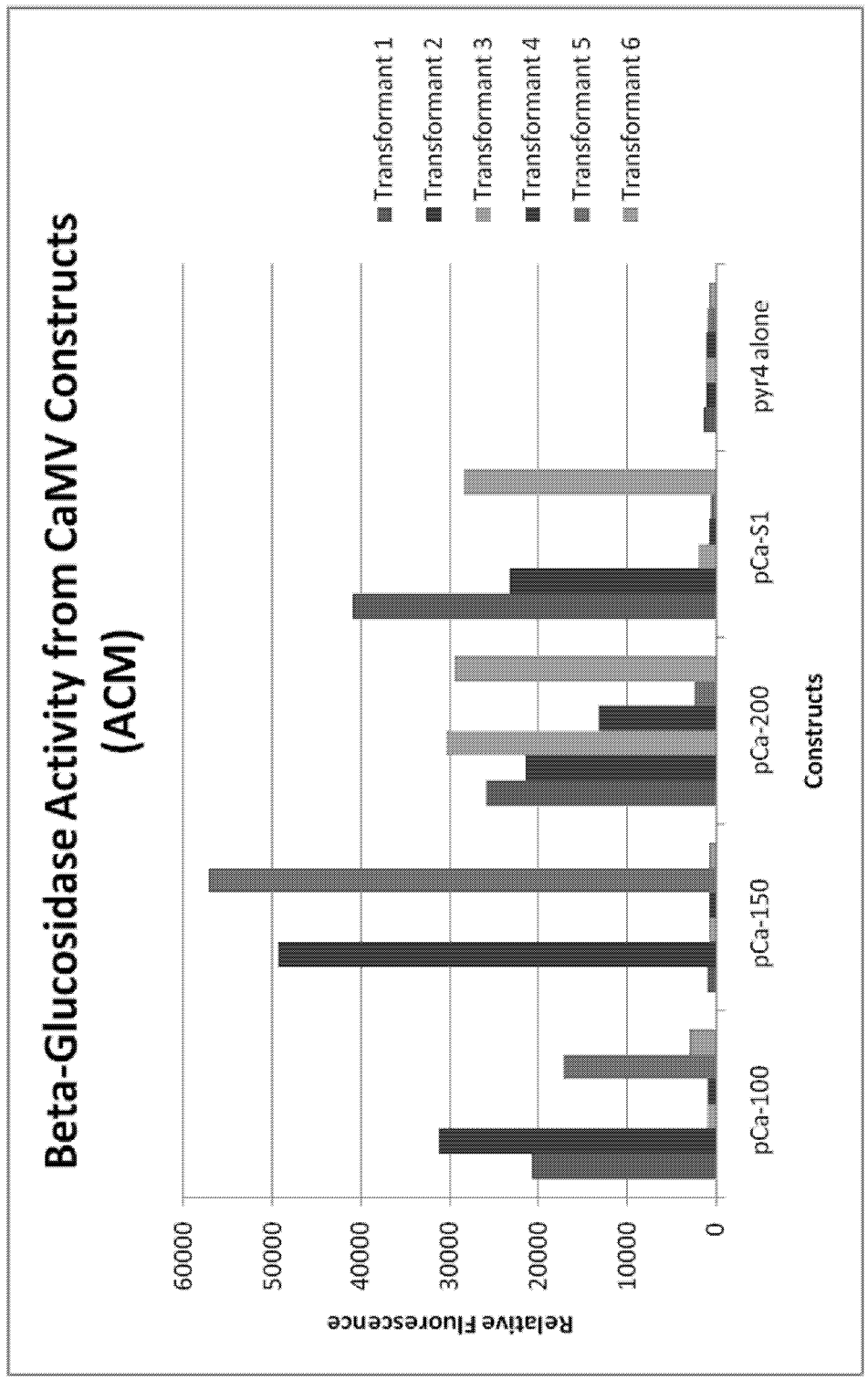
Figure 6B:
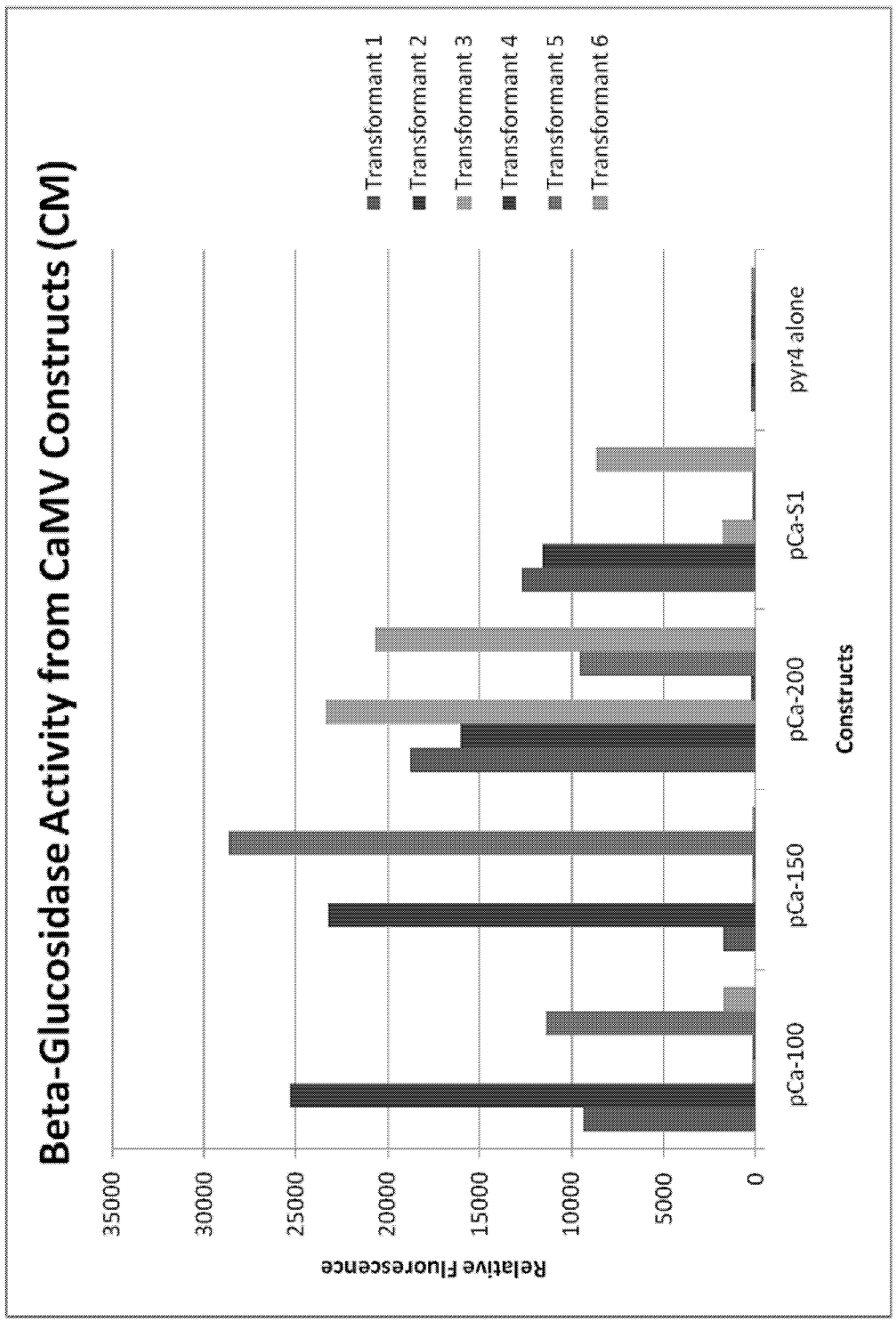

FIG. 5A-5D provides schematic maps of vectors useful in practicing the present invention. FIG. 5A illustrates a vector, referred to as pCa-S1, comprising a CaMV 35S promoter, a 5'UTR sequence corresponding to the native CaMV S1 leader region (CaMV S1 5'UTR), and a polypeptide coding sequence of a *Cochliobolus heterostrophus* β-glucosidase gene, a terminator sequence from the *Trichoderma reesei* CBHI gene, which includes a 3' UTR, and a selectable marker (pyr). FIG. 5B illustrates a vector, referred to as pCa-100, comprising a CaMV 35S promoter, a 5'UTR sequence corresponding to 100 base pairs (bp) sequence from the 5'UTR of the *Trichoderma reesei* glyceraldehyde-3-phosphate dehydrogenase (gpd) gene (100 bp 5' UTR from gpd), a polypeptide coding sequence of a *Cochliobolus heterostrophus* β-glucosidase gene, a terminator sequence from the *Trichoderma reesei* CBHI gene, which includes a 3' UTR, and a selectable marker (pyr). FIG. 5C illustrates a vector, referred to as pCa-150, comprising a CaMV 35S promoter, a 5'UTR sequence corresponding to 150 base pairs (bp) sequence from the 5'UTR of the *Trichoderma reesei* glyceraldehyde-3-phosphate dehydrogenase (gpd) gene (150 bp 5' UTR from gpd), a polypeptide coding sequence of a *Cochliobolus heterostrophus* β-glucosidase gene, a terminator sequence from the *Trichoderma reesei* CBHI gene, which includes a 3' UTR, and a selectable marker (pyr). FIG. 5D illustrates a vector, referred to as pCa-200, comprising a CaMV 35S promoter, a 5'UTR sequence corresponding to 200 base pairs (bp) sequence from the 5'UTR of the *Trichoderma reesei* glyceraldehyde-3-phosphate dehydrogenase (gpd) gene (200 bp 5' UTR from gpd), a polypeptide coding sequence of a *Cochliobolus heterostrophus* β-glucosidase gene, a terminator sequence from the *Trichoderma reesei* CBHI gene, which includes a 3' UTR, and a selectable marker (pyr); and FIG. 6A-B provides graphs of β-glucosidase activity (in relative units) in 7 separate isolates of a *Trichoderma reesei* strain MCG80 transformed with one of pCa-S1, pCa-100, pCa-150, or pCa-200, compared to isolates of the parent *Trichoderma reesei* strain transformed with a vector carrying a selectable marker but without an expression cassette (MCG80pyr4+). FIG. 6A provides results for strains tested in *Aspergillus* Complete Medium. FIG. 6B provides results for strains tested in Complete Medium.

4. DETAILED DESCRIPTION

Applicants have discovered that promoters that are active in plants are useful for expressing genes of interest in filamentous fungi and that, when combined with 5' untranslated regions (5'UTR), can significantly increase the yield of active polypeptide expressed in a filamentous fungal cell. Consequently, provided herein, are expression cassettes comprising four components, operably linked in a 5' to 3' direction: a promoter that is active in a plant, a 5' UTR, a polypeptide coding sequence, and a 3' UTR. These expression cassettes, described in more detail below, can be transformed into filamentous fungal cells and permit the production and recovery of polypeptides of interest. Accordingly, the present disclosure provides expression cassettes, vectors comprising expression cassettes or components thereof, filamentous fungal cells bearing expression cassettes, and methods of producing, recovering and purifying polypeptides of interest from the filamentous fungal cells described herein.

4.1. Expression Cassette

The expression cassette of the present disclosure typically comprises, operably linked in a 5' to 3' direction: (a) a promoter active in a plant, (b) a 5' untranslated region, (c) a coding sequence, and (4) a 3' untranslated region, features and examples of which are described further herein below.

4.1.1. Promoter Sequences

The promoters useful in the expression cassettes described herein are promoters that are active in plants. The promoter can be a plant promoter, i.e., a promoter that is native to a plant genome, or a promoter from a plant virus. Collectively they are referred to herein as "plant promoters."

The plant promoters are preferably strong constitutive promoters, e.g., promoters that have at least 20% of the activity of the *T. reesei* CBHI promoter in a filamentous fungus such as *T. reesei*. Promoter activity can be assayed by comparing reporter protein (e.g., green fluorescent protein ("GFP")) production by filamentous fungal cells (e.g., *T. reesei* cells) transformed with a vector (e.g., pW as described in the Examples below) containing the test promoter operably linked to the reporter protein coding sequence (the "test vector") relative to filamentous fungal cells transformed with vector in which the test promoter is substituted with the CBHI promoter (the "control" vector). Reporter protein expression is measured or compared in filamentous fungal cells transformed with the test vector and in filamentous fungal cells transformed with the control vector grown under suitable growth conditions, e.g., in minimal medium containing 2% lactose as described in Murray et al., 2004, Protein Expression and Purification 38:248-257 and Ilmen et al., 1997, Appl. Environmental Microbiol. 63(4):1298-1306. The promoter of interest is considered to be a strong promoter if reporter protein expression in filamentous fungal cells transformed with the test vector is at least about 20% the level of reporter expression observed in the filamentous fungal cells transformed with the control vector. A promoter that can be used in accordance with the present disclosure can, in specific embodiments, have at least 20%, at least 30%, at least 40%, at least 50%, at least 60%, or at least 75% the activity of the CBHI promoter in the assay described above.

Plant promoter may be from a monocotyledonous or a dicotyledonous plant. Numerous plant promoters are known, including promoters from such plants as potato, rice, corn, wheat, tobacco or barley.

Promoters useful in the expression cassettes provided herein also include plant viral promoters. Such promoters can be from any family of plant virus, including but not limited to viruses belong to one of the Caulimoviridae, Geminiviridae, Reoviridae, Rhabdoviridae, Virgaviridae, Alphaflexiviridae, Potyviridae, Betaflexiviridae, Closteroviridae, Tymoviridae, Luteoviridae, Tombusviridae, Sobemoviruses, Neopviruses, Secoviridae and Bromoviridae families.

The promoter, whether from a plant or a plant virus, is preferably constitutively active. Exemplary constitutive promoters include the cauliflower mosaic virus (CaMV) 35S promoter (Odell et al., 1985, Nature 313:810-812); *Arabidopsis* At6669 promoter, maize Ubi 1 (Christensen et al., 1992, Plant Sol. Biol. 18:675-689); rice actin (McElroy et al., 1990, Plant Cell 2:163-171); pEMU (Last et al., 1991, Theor. Appl. Genet. 81:581-588); and Synthetic Super MAS (Ni et al., 1995, The Plant Journal 7: 661-76), the CaMV 19S promoter; Commelina yellow mottle virus ("CoYMV") promoter; Figwort Mosaic Virus (FMV) promoter (Richins et al., 1987, Nucleic Acids Res. 20:8451); cassaya vein mosaic virus (Cs-VMV) promoter; Strawberry Vein Banding Virus transcript promoter (Wang et al., 2000, Virus Genes 20:11-17; Genbank X97304); and Mirabilis Mosaic Caulimovirus full-length transcript promoter (U.S. Pat. No. 6,420,547; Dey and Maiti, 1999, Transgenics 3:61-70). Other constitutive promoters include those in U.S. Pat. Nos. 5,659,026, 5,608,149; 5,608, 144; 5,604,121; 5,569,597: 5,466,785; 5,399,680; 5,268,463; 5,608,142; and 7,906,705.

In preferred embodiments, the constitutive promoter is a CaMV 35S promoter (see, e.g., Accession no. 551061, Cooke et al., 1990, Plant Mol. Biol. 14 (3), 391-405), including the enhanced CaMV 35S promoter (see, for example U.S. Pat. No. 5,106,739)).

In certain aspects, the promoter is a CaMV 35S promoter comprising a nucleotide sequence corresponding to SEQ ID NO:1, or a promoter comprising a nucleotide sequence having at least 70%, 75%, 80%, 85%, 90%, 95%, 96%, 97%, 98%, or 99% sequence identity to SEQ ID NO:1.

In other aspects, the promoter is a CoYMV promoter comprising a nucleotide sequence corresponding to SEQ ID NO:2, or a promoter comprising a nucleotide sequence having at least 70%, 75%, 80%, 85%, 90%, 95%, 96%, 97%, 98%, or 99% sequence identity to SEQ ID NO:2.

4.1.2. 5' Untranslated Region (5' UTR)

Expression cassettes of the present disclosure further comprise, operably linked at the 3' end of the promoter, a sequence that corresponds to a 5' untranslated region (5' UTR) in the mRNA resulting from transcription of the expression cassette that is operable in filamentous fungi (for convenience referred to as a "5' UTR" in the expression cassette). The 5' UTR can comprise a transcription start site and other features that increase transcription or translation, such as a ribosome binding site.

The 5' UTR can range in length, from about 50 nucleotides to about 500 nucleotides. In some embodiments, the 5' UTR is about 50 nucleotides, about 100 nucleotides, about 150 nucleotides, about 200 nucleotides, about 250 nucleotides, about 300 nucleotides, about 350 nucleotides, about 400 nucleotides, about 450 nucleotides, or about 500 nucleotides in length.

The 5' UTR of the expression cassette can be derived from any number of sources, including from a plant gene, a plant virus gene, a fungal, including a filamentous fungal, gene. The 5' UTR can comprise a nucleotide sequence corresponding to all of a fragment of a 5'UTR from a plant gene, a plant viral gene, or a filamentous fungal gene. The 5' UTR can comprise a nucleotide sequence corresponding to all or a fragment of the 5' UTR of a gene encoding a first polypeptide coding sequence of the expression cassette. Where the 5' UTR of the expression cassette is derived from a plant gene or a plant viral gene 5' UTR, it may be from the same or from a different species as the promoter.

The 5' UTR of the expression cassette of the disclosure can suitably include a nucleotide sequence corresponding to all or a fragment of a 5' UTR from a plant gene or a plant viral gene, including but not limited to a gene native to a virus belonging to one of the Caulimoviridae, Geminiviridae, Reoviridae, Rhabdoviridae, Virgaviridae, Alphaflexiviridae, Potyviridae, Betaflexiviridae, Closteroviridae, Tymoviridae, Luteoviridae, Tombusviridae, Sobemoviruses, Neopviruses, Secoviridae and Bromoviridae families. In some embodiments, the 5' UTR comprises a nucleotide sequence corresponding to all or a fragment of a 5' UTR from a Caulimoviridae virus. In specific embodiments, the 5' UTR comprises a nucleotide sequence corresponding to all or a fragment of a CaMV S1 5'UTR. In a specific example, the 5' UTR comprises the nucleotide sequence of SEQ ID NO:3, or a nucleotide sequence having at least 70%, 75%, 80%, 85%, 90%, 95%, 96%, 97%, 98%, or 99% sequence identity to SEQ ID NO:3.

The 5' UTR of the expression cassette of the disclosure can suitably include a nucleotide sequence corresponding to all or a fragment of a 5' UTR from a filamentous fungal gene. Where the 5' UTR is derived from a filamentous fungal gene, it may be from a gene native to the filamentous fungal species in which the expression construct is intended to operate. In some embodiments, the 5' UTR comprises a nucleotide sequence corresponding to all or a fragment of a gene native to an *Aspergillus, Trichoderma, Chrysosporium, Cephalosporium, Neurospora, Podospora, Endothia, Cochiobolus, Pyricularia, Rhizomucor, Hansenula, Humicola, Mucor, Tolypocladium, Fusarium, Penicillium, Talaromyces, Emericella, Hypocrea, Acremonium, Aureobasidium, Beauveria, Cephalosporium, Ceriporiopsis, Chaetomium, Paecilomyces, Claviceps, Cryptococcus, Cyathus, Gilocladium, Magnaporthe, Myceliophthora, Myrothecium, Phanerochaete, Paecilomyces, Rhizopus, Schizophylum, Stagonospora, Thermomyces, Thermoascus, Thielavia, Trichophyton, Trametes,* or *Pleurotus* species.

Exemplary filamentous fungal species from which the 5' UTRs can be derived include *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum, Phanerochaete chrysosporium, Phlebia radiate, Pleurotus eryngii, Thielavia terrestris, Trichoderma harzianum, Trichoderma longibrachiatum, Trichoderma reesei,* and *Trichoderma viride*.

In certain embodiments, the 5' UTR comprises a nucleotide sequence corresponding to all or a fragment of the 5' UTR from a gene native to *Trichoderma reesei*, such as the *Trichoderma reesei* cbh1, cbh2, egl1, egl2, eg15, xln1 and xln2 genes. In exemplary embodiments, the 5' UTR comprises a nucleotide sequence corresponding to a fragment of the 5' UTR of the glyceraldehyde-3-phosphate dehydrogenase (gpd) gene of *Trichoderma reesei*, for example, a 100 nucleotide fragment (e.g. SEQ ID NO:4), 150 nucleotide fragment (e.g. SEQ ID NO:5), or a 200 nucleotide fragment (e.g. SEQ ID NO:6) of the *Trichoderma reesei* gpd gene. In some embodiments, the 5' UTR of the expression cassette comprises a nucleotide sequence having at least 70%, 75%, 80%, 85%, 90%, 95%, 96%, 97%, 98%, or 99% sequence identity to any one of SEQ ID NO:4, SEQ ID NO:5, or SEQ ID NO:6.

4.1.3. Polypeptide Coding Sequences

The expression cassettes described herein are intended to allow expression of any polypeptide of interest ("POI") in filamentous fungal cells. As such, the identity of the polypeptide coding sequence is not limited to any particular type of polypeptide or to polypeptides from any particular source. It can be eukaryotic or prokaryotic. The polypeptide coding sequence can be from a gene native to the recombinant filamentous fungal cell into which the expression cassette is intended to be introduced (e.g., from a filamentous fungus such as *Trichoderma reesei* or *Aspergillus niger*) or heterologous to the recombinant filamentous fungal cell into which the expression cassette is intended to be introduced (e.g., from a plant, animal, virus, or non-filamentous fungus).

The POI coding sequence can encode an enzyme such as a carbohydrase, such as a liquefying and saccharifying α-amylase, an alkaline α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, subtilisin, thermolysin, an aspartic proteinase, or trypsin; a lipase or esterase, such as a triglyceridase, a phospholipase, acyl transferase, a pregastric esterase, a phosphatase, a phytase, an amidase, an iminoacylase, a glutaminase, a lysozyme, or a penicillin acylase; an isomerase such as glucose isomerase; an oxidoreductases, e.g., an amino acid oxidase, a catalase, a chloroperoxidase, a glucose oxidase, a hydroxysteroid dehydrogenase or a peroxidase; a lyase such as a acetolactate decarboxylase, an aspartic β-decarboxylase, a fumarese or a histadase; a transferase such as cyclodextrin glycosyltransferase; or a ligase, for example.

In particular embodiments, the enzyme is an aminopeptidase, a carboxypeptidase, a chitinase, a cutinase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase.

In other particular embodiments, the enzyme is an α-amylase, a cellulase; an α-glucosidase, an α-galactosidase, a glucoamylase, a hemicellulase, a xylanase, a pectinase, a pullulanase; an acid protease, an alkali protease, an aspartic proteinase, a lipase, a cutinase or a phytase. In certain aspects, the POI is a cellulase another protein useful in a cellulotyic reaction, for example a hemicellulase or an accessory polypeptide. Cellulases are known in the art as enzymes that hydrolyze cellulose (β-1,4-glucan or β D-glucosidic linkages) resulting in the formation of glucose, cellobiose, cellooligosaccharides, and the like. Cellulase enzymes have been traditionally divided into three major classes: endoglucanases ("EG"), exoglucanases or cellobiohydrolases (EC 3.2.1.91) ("CBH") and β-glucosidases (EC 3.2.1.21) ("BG") (Knowles et al., 1987, TIBTECH 5:255-261; Schulein, 1988, Methods in Enzymology 160(25):234-243). Accessory proteins Endoglucanases: Endoglucanases break internal bonds and disrupt the crystalline structure of cellulose, exposing individual cellulose polysaccharide chains ("glucans"). Endoglucanases include polypeptides classified as Enzyme Commission no. ("EC") 3.2.1.4) or which are capable of catalyzing the endohydrolysis of 1,4-β-D-glucosidic linkages in cellulose, lichenin or cereal β-D-glucans. Enzyme Commission numbering is a numerical classification scheme for enzymes.

Examples of suitable bacterial endoglucanases include, but are not limited to, *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of suitable fungal endoglucanases include, but are not limited to, *Trichoderma reesei* endoglucanase I (Penttila et al., 1986, Gene 45: 253-263; GenBank accession no. M15665); *Trichoderma reesei* endoglucanase II (Saloheimo et al., 1988, Gene 63:11-22; GenBank accession no. M19373); *Trichoderma reesei* endoglucanase III (Okada et al., 1988, Appl. Environ. Microbiol. 64: 555-563; GenBank accession no. AB003694); *Trichoderma reesei* endoglucanase IV (Saloheimo et al., 1997, Eur. J. Biochem. 249: 584-591; GenBank accession no. Y11113); and *Trichoderma reesei* endoglucanase V (Saloheimo et al., 1994, Molecular Microbiology 13: 219-228; GenBank accession no. Z33381); *Aspergillus aculeatus* endoglucanase (Ooi et al., 1990, Nucleic Acids Research 18: 5884); *Aspergillis kawachii* endoglucanase (Sakamoto et al., 1995, Current Genetics 27: 435-439); *Chrysosporium* sp. C1 endoglucanase (U.S. Pat. No. 6,573,086; GenPept accession no. AAQ38150); *Corynascus heterothallicus* endoglucanase (U.S. Pat. No. 6,855,531; GenPept accession no. AAY00844); *Erwinia carotovara* endoglucanase (Saarilahti et al., 1990, Gene 90: 9-14); *Fusarium oxysporum* endoglucanase (GenBank accession no. L29381); *Humicola grisea* var. *thermoidea* endoglucanase (GenBank accession no. AB003107); *Melanocarpus albomyces* endoglucanase (GenBank accession no. MAL515703); *Neurospora crassa* endoglucanase (GenBank accession no. XM.sub.—324477); *Piromyces equi* endoglucanase (Eberhardt et al., 2000, Microbiology 146: 1999-2008; GenPept accession no. CAB92325); *Rhizopus oryzae* endoglucanase (Moriya et al., 2003, J. Bacteriology 185: 1749-1756; GenBank accession nos. AB047927, AB056667, and AB056668); and *Thielavia terrestris* endoglucanase (WO 2004/053039; EMBL accession no. CQ827970).

Cellobiohydrolases: Cellobiohydrolases incrementally shorten the glucan molecules, releasing mainly cellobiose units (a water-soluble β-1,4-linked dimer of glucose) as well as glucose, cellotriose, and cellotetraose. Cellobiohydrolases include polypeptides classified as EC 3.2.1.91 or which are capable of catalyzing the hydrolysis of 1,4-β-D-glucosidic linkages in cellulose or cellotetraose, releasing cellobiose from the ends of the chains. Exemplary cellobiohydrolases include *Trichoderma reesei* cellobiohydrolase I (CEL7A) (Shoemaker et al., 1983, Biotechnology (N.Y.) 1: 691-696); *Trichoderma reesei* cellobiohydrolase II (CEL6A) (Teeri et al., 1987, Gene 51: 43-52); *Chrysosporium lucknowense* CEL7 cellobiohydrolase (WO 2001/79507); *Myceliophthora thermophila* CEL7 (WO 2003/000941); and *Thielavia terrestris* cellobiohydrolase (WO 2006/074435).

β-Glucosidases: β-Glucosidases split cellobiose into glucose monomers. β-glucosidases include polypeptides classified as EC 3.2.1.21 or which are capable of catalyzing the hydrolysis of terminal, non-reducing β-D-glucose residues with release of β-D-glucose. Exemplary β-glucosidases can be obtained from *Cochliobolus heterostrophus* (SEQ ID NO:34), *Aspergillus oryzae* (WO 2002/095014), *Aspergillus fumigatus* (WO 2005/047499), *Penicillium brasilianum* (e.g., *Penicillium brasilianum* strain IBT 20888) (WO 2007/019442), *Aspergillus niger* (Dan et al., 2000, J. Biol. Chem. 275: 4973-4980), *Aspergillus aculeatus* (Kawaguchi et al., 1996, Gene 173: 287-288), *Penicilium funiculosum* (WO 2004/078919), *S. pombe* (Wood et al., 2002, Nature 415: 871-880), *T. reesei* (e.g., β-glucosidase 1 (U.S. Pat. No. 6,022,725), β-glucosidase 3 (U.S. Pat. No. 6,982,159), β-glucosidase 4 (U.S. Pat. No. 7,045,332), β-glucosidase 5 (U.S. Pat. No. 7,005,289), β-glucosidase 6 (U.S. Publication No. 20060258554), or β-glucosidase 7 (U.S. Publication No. 20060258554)).

Hemicellulases: A POI can be any class of hemicellulase, including an endoxylanase, a β-xylosidase, an α-L-arabinofuranosidase, an α-D-glucuronidase, an acetyl xylan esterase, a feruloyl esterase, a coumaroyl esterase, an α-galactosidase, a α-galactosidase, a β-mannanase or a β-mannosidase.

Endoxylanases suitable as POIs include any polypeptide classified EC 3.2.1.8 or which is capable of catalyzing the endohydrolysis of 1,4-β-D-xylosidic linkages in xylans. Endoxylanases also include polypeptides classified as EC 3.2.1.136 or which are capable of hydrolyzing 1,4 xylosidic linkages in glucuronoarabinoxylans.

β-xylosidases include any polypeptide classified as EC 3.2.1.37 or which is capable of catalyzing the hydrolysis of 1,4-β-D-xylans to remove successive D-xylose residues from the non-reducing termini β-xylosidases may also hydrolyze xylobiose.

α-L-arabinofuranosidases include any polypeptide classified as EC 3.2.1.55 or which is capable of acting on α-L-arabinofuranosides, α-L-arabinans containing (1,2) and/or (1,3)- and/or (1,5)-linkages, arabinoxylans or arabinogalactans.

α-D-glucuronidases include any polypeptide classified as EC 3.2.1.139 or which is capable of catalyzing a reaction of the following form: α-D-glucuronoside+H(2)O=an alcohol+D-glucuronate. α-D-glucuronidases may also hydrolyse 4-O-methylated glucoronic acid, which can also be present as a substituent in xylans. α-D-glucuronidases also include polypeptides classified as EC 3.2.1.131 or which are capable of catalying the hydrolysis of α-1,2-(4-O-methyl)glucuronosyl links.

Acetyl xylan esterases include any polypeptide classified as EC 3.1.1.72 or which is capable of catalyzing the deacetylation of xylans and xylo-oligosaccharides. Acetyl xylan esterases may catalyze the hydrolysis of acetyl groups from polymeric xylan, acetylated xylose, acetylated glucose, α-napthyl acetate or p-nitrophenyl acetate but, typically, not from triacetylglycerol. Acetyl xylan esterases typically do not act on acetylated mannan or pectin.

Feruloyl esterases include any polypeptide classified as EC 3.1.1.73 or which is capable of catalyzing a reaction of the form: feruloyl-saccharide+H(2)O=ferulate+saccharide. The saccharide may be, for example, an oligosaccharide or a polysaccharide. A feruloyl esterase may catalyze the hydrolysis of the 4-hydroxy-3-methoxycinnamoyl (feruloyl) group from an esterified sugar, which is usually arabinose in natural substrates, while p-nitrophenol acetate and methyl ferulate are typically poorer substrates. Feruloyl esterase are sometimes considered hemicellulase accessory enzymes, since they may help xylanases and pectinases to break down plant cell wall hemicellulose and pectin.

Coumaroyl esterases include any polypeptide classified as EC 3.1.1.73 or which is capable of catalyzing a reaction of the form: coumaroyl–saccharide+H(2)O=coumarate+saccharide. The saccharide may be, for example, an oligosaccharide or a polysaccharide. Because some coumaroyl esterases are classified as EC 3.1.1.73 they may also be referred to as feruloyl esterases.

α-galactosidases include any polypeptide classified as EC 3.2.1.22 or which is capable of catalyzing the hydrolysis of terminal, non-reducing α-D-galactose residues in α-D-galactosides, including galactose oligosaccharides, galactomannans, galactans and arabinogalactans. α-galactosidases may also be capable of hydrolyzing α-D-fucosides.

β-galactosidases include any polypeptide classified as EC 3.2.1.23 or which is capable of catalyzing the hydrolysis of terminal non-reducing β-D-galactose residues in β-D-galactosides. β-galactosidases may also be capable of hydrolyzing α-L-arabinosides.

β-mannanases include any polypeptide classified as EC 3.2.1.78 or which is capable of catalyzing the random hydrolysis of 1,4-β-D-mannosidic linkages in mannans, galactomannans and glucomannans.

β-mannosidases include any polypeptide classified as EC 3.2.1.25 or which is capable of catalyzing the hydrolysis of terminal, non-reducing β-D-mannose residues in β-D-mannosides.

Suitable hemicellulases include *T. reesei* α-arabinofuranosidase I (ABF1), α-arabinofuranosidase II (ABF2), α-arabinofuranosidase III (ABF3), α-galactosidase I (AGL1), α-galactosidase II (AGL2), α-galactosidase III (AGL3), acetyl xylan esterase I (AXE1), acetyl xylan esterase III (AXE3), endoglucanase VI (EG6), endoglucanase VIII (EG8), α-glucuronidase I (GLR1), β-mannanase (MAN1), polygalacturonase (PEC2), xylanase I (XYN1), xylanase II (XYN2), xylanase III (XYN3), and β-xylosidase (BXL1).

Accessory Polypeptides: Accessory polypeptides are present in cellulase preparations that aid in the enzymatic digestion of cellulose (see, e.g., WO 2009/026722 and Harris et al., 2010, Biochemistry, 49:3305-3316). In some embodiments, the accessory polypeptide is an expansin or swollenin-like protein. Expansins are implicated in loosening of the cell wall structure during plant cell growth (see, e.g., Salheimo et al., 2002, Eur. J. Biochem., 269:4202-4211). Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein, contains an N-terminal Carbohydrate Binding Module Family 1 domain (CBD) and a C-terminal expansin-like domain. In some embodiments, an expansin-like protein and/or swollenin-like protein comprises one or both of such domains and/or disrupts the structure of cell walls (e.g., disrupting cellulose structure), optionally without producing detectable amounts of reducing sugars. Other types of accessory proteins include cellulose integrating proteins, scaffoldins and/or a scaffoldin-like proteins (e.g., CipA or CipC from *Clostridium thermocellum* or *Clostridium cellulolyticum* respectively). Other exemplary accessory proteins are cellulose induced proteins and/or modulating proteins (e.g., as encoded by cip1 or cip2 gene and/or similar genes from *Trichoderma reesei*; see e.g., Foreman et al., 2003, J. Biol. Chem., 278:31988-31997.

The POI coding sequence of an expression cassette of the disclosure can also encode a therapeutic polypeptide (i.e., a polypeptide having a therapeutic biological activity). Examples of suitable therapeutic polypeptides include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Antibodies, e.g., monoclonal antibodies (including but not limited to chimeric and humanized antibodies), are of particular interest.

In a further embodiment, the POI coding sequence can encode a reporter polypeptide. Such reporter polypeptides may be optically detectable or colorigenic, for example. In this embodiment, the polypeptide may be a β-galactosidase (lacZ), β-glucuronidase (GUS), luciferase, alkaline phosphatase, nopaline synthase (NOS), chloramphenicol acetyltransferase (CAT), horseradish peroxidase (HRP) or a fluorescent protein green, e.g., green fluorescent protein (GFP), or a derivative thereof.

Where the POI coding sequence is from a eukaryotic gene, the polypeptide coding sequence can, but need not, include introns which can be spliced out during post-transcriptional processing of the transcript in the cell.

For some applications, it may be desirable for the polypeptide produced to be secreted by the filamentous fungal cell. For such application, the POI coding sequence can include, or be engineered to include, a signal sequence encoding a leader peptide that directs the POI to the filamentous fungal cell's secretory pathway. The signal sequence, when present, is in an appropriate translation reading frame with the mature POI coding sequence. Accordingly, the POI coding sequence can further encode a signal sequence operably linked to the N-terminus of the POI, where the signal sequence contains a sequence of amino acids that directs the POI to the secretory system of the recombinant filamentous fungal cell, resulting in secretion of the mature POI from the recombinant filamentous fungal cell into the medium in which the recombinant filamentous fungal cell is growing. The signal sequence is cleaved from the fusion protein prior to secretion of the mature POI. The signal sequence employed can be endogenous or non-endogenous to the POI and/or the recombinant filamentous fungal cell. Preferably, the signal sequence is a signal sequence that facilitates protein secretion from a filamentous fungal (e.g., *Trichoderma* or *Aspergillus*) cell and can be the signal sequence of a protein that is known to be highly secreted from filamentous fungi. Such signal sequences include, but are not limited to: the signal sequence of cellobiohydrolase I, cellobiohydrolase II, endoglucanase I, endoglucanase II, endoglucanase III, α-amylase, aspartyl proteases, glucoamylase, mannanase, glycosidase and barley endopeptidase B (see Saarelainen, 1997, Appl. Environ. Microbiol. 63:4938-4940), for example. Specific examples include the signal sequence from *Aspergillus oryzae* TAKA alpha-amylase, *Aspergillus niger* neutral alpha-amylase, *Aspergillus niger glucoamylase, Rhizomucor miehei* aspartic proteinase, *Humicola insolens* cellulase, and *Humicola lanuginosa* lipase. Other examples of signal sequences are those originating from the α-factor gene of a yeast (e.g., *Saccharomyces, Kluyveromyces* and *Hansenula*) or a *Bacillus* α-amylase. In certain embodiments, therefore, the POI coding sequence includes a sequence encoding a signal sequence, yielding a POI in the form of a polypeptide comprising an N-terminal signal sequence for secretion of the protein from the recombinant filamentous fungal cell.

In certain embodiments, the POI coding sequence can encode a fusion protein. In addition to POIs comprising signal sequences as described above, the fusion protein can further contain a "carrier protein," which is a portion of a protein that is endogenous to and highly secreted by the filamentous fungal cell. Suitable carrier proteins include those of *Trichoderma reesei* mannanase I (Man5A, or MAN1), *Trichoderma reesei* cellobiohydrolase II (Ce16A, or CBHII) (see, e.g., Paloheimo et al., 2003, Appl. Environ. Microbiol. 69(12): 7073-7082) or *Trichoderma reesei* cellobiohydrolase I (CBHI). In one embodiment, the carrier protein is a truncated *Trichoderma reesei* CBHI protein that includes the CBHI core region and part of the CBHI linker region. An expression cassette of the disclosure can therefore include a coding sequence for a fusion protein containing, from the N-terminus to the C-terminus, a signal sequence, a carrier protein and a POI in operable linkage.

In certain embodiments, the POI coding sequence can be codon optimized for expression of the protein in a particular filamentous fungal cell. Since codon usage tables listing the usage of each codon in many cells are known in the art (see, e.g., Nakamura et al., 2000, Nucl. Acids Res. 28:292) or readily derivable, such coding sequence can be readily designed.

The expression cassettes described herein comprise at least a first polypeptide coding sequence encoding a first polypeptide, but may optionally comprise second, third, fourth, etc. polypeptide coding sequences encoding second, third, fourth, etc. polypeptides.

4.1.4. 3' Untranslated Region (3' UTR)

Expression cassettes of the present disclosure further comprise, operably linked at the 3' end of the first, and any optional additional, polypeptide coding sequence, a sequence that corresponds to a 3' untranslated region (3' UTR) in the mRNA resulting from transcription of the expression cassette (for convenience referred to as a "3' UTR" in the expression cassette). The 3' UTR of the expression cassette comprises at least a polyadenylation signal, directing cleavage and polyadenylation of the transcript. The 3' UTR can optionally comprise other features important for nuclear export, translation, and/or stability of the mRNA, such as for example, a termination signal.

The 3' UTR can range in length from about 50 nucleotides to about 2000 or nucleotides or longer. In some embodiments, the 5' UTR is about 50 nucleotides, about 100 nucleotides, about 150 nucleotides, about 200 nucleotides, about 250 nucleotides, about 300 nucleotides, about 350 nucleotides, about 400 nucleotides, about 450 nucleotides, about 500 nucleotides, about 600 nucleotides, about 700 nucleotides, about 800 nucleotides, about 900 nucleotides, about 1000 nucleotides, or about 2000 nucleotides in length or more.

Suitable 3' UTRs for use in the expression cassettes of the present disclosure can be derived from any number of sources, including from a plant gene, a plant virus gene, a yeast gene, a filamentous fungal, gene, or a gene encoding the POI. The 3' UTR can comprise a nucleotide sequence corresponding to all or a fragment of a 3'UTR from a plant gene, a plant viral gene, a yeast gene or a filamentous fungal gene. The 3' UTR can comprise a nucleotide sequence corresponding to all or a fragment of the 3' UTR of a gene encoding a first, second, or further polypeptide coding sequence of the expression cassette. The 3' UTR can be from the same or a different species as one other component in the expression cassette (e.g., the promoter or the polypeptide coding sequence). The 3' UTR can be from the same species as the filamentous fungal cell in which the expression construct is intended to operate.

The 3' UTR of an expression cassette of the disclosure may also suitably be derived from a plant gene or a plant viral gene, for example a gene native to a virus belonging to one of the Caulimoviridae, Geminiviridae, Reoviridae, Rhabdoviridae, Virgaviridae, Alphaflexiviridae, Potyviridae, Betaflexiviridae, Closteroviridae, Tymoviridae, Luteoviridae, Tombusviridae, Sobemoviruses, Neopviruses, Secoviridae and Bromoviridae families. In some embodiments, the 3' UTR comprises a nucleotide sequence corresponding to all or a fragment of a 3' UTR from a Caulimoviridae virus. In specific embodiments, the 3' UTR comprises a nucleotide sequence corresponding to all or a fragment of a CaMV 35S transcript 3'UTR.

The 3' UTR of an expression cassette of the disclosure may also suitably be derived from a mammalian gene or a mammalian viral gene, for example a gene native to a virus belonging to one of the viruses belong to one of the Retroviridae, Picornaviridae, Calciviridae, Togaviridae, Flaviridae, Coronaviridae, Rhabdoviridae, Filoviridae, Paramyxoviridae, Orthomyxoviridae, Bungaviridae, Arenaviridae, Reoviridae, Birnaviridae, Hepadnaviridae, Parvoviridae, Papovaviridae, Adenoviridae, Herpesviridae, Polyomaviridae, Poxyiridae and Iridoviridae families.

The 3' UTR of an expression cassette of the disclosure may also suitably be derived from a filamentous fungal gene. Where the 3' UTR is derived from a filamentous fungal gene, it may be from a gene native to the filamentous fungal species in which the expression construct is intended to operate. Exemplary filamental fungal species the 3' UTR comprises a nucleotide sequence corresponding to all or a fragment of a gene native to a *Aspergillus, Trichoderma, Chrysosporium, Cephalosporium, Neurospora, Podospora, Endothia, Cochiobolus, Pyricularia, Rhizomucor, Hansenula, Humicola, Mucor, Tolypocladium, Fusarium, Penicillium, Talaromyces, Emericella, Hypocrea, Acremonium, Aureobasidium, Beauveria, Cephalosporium, Ceriporiopsis, Chaetomium, Paecilomyces, Claviceps, Cryptococcus, Cyathus, Gilocladium, Magnaporthe, Myceliophthora, Myrothecium, Phanerochaete, Paecilomyces, Rhizopus, Schizophylum, Stagonospora, Thermomyces, Thermoascus, Thielavia, Trichophyton, Trametes*, and *Pleurotus* species.

Species of filamentous fungi from which the 3' UTR can be derived include *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum, Phanerochaete chrysosporium, Phlebia radiate, Pleurotus eryngii, Thielavia terrestris, Trichoderma harzianum, Trichoderma longibrachiatum, Trichoderma reesei,* and *Trichoderma viride.*

In a specific embodiment, the 3' UTR comprises a nucleotide sequence corresponding to all or a fragment of the 3' UTR from a gene native to *Trichoderma reesei*, such as the *Trichoderma reesei* CBHI, cbh2, egl1, egl2, egl5, xln1 and xln2 genes. In an exemplary embodiment, the 3' UTR comprises a nucleotide sequence corresponding to a fragment of the 3' UTR of the glyceraldehyde-3-phosphate dehydrogenase (gpd) gene of *Trichoderma reesei*. In another exemplary embodiment, the 3' UTR comprises the nucleotide sequence of all or a fragment of the 3' UTR of a gene encoding CBHI.

In other exemplary embodiments, the 3' UTR comprises a nucleotide sequence corresponding to all or a fragment of the 3'UTR from an *Aspergillus niger* or *Aspergillus awamori* glucoamylase gene (Nunberg et al., 1984, Mol. Cell. Biol. 4:2306-2315 and Boel et al., 1984, EMBO Journal, 3:1097-1102), an *Aspergillus nidulans* anthranilate synthase gene, an *Aspergillus oryzae* TAKA amylase gene, or the *Aspergillus nidulans* trpc gene (Punt et al., 1987, Gene 56:117-124).

In yet other exemplary embodiments, the 3' UTR comprises the nucleotide sequence corresponding to all or a fragment of a 3' UTR from a *Cochliobolus* species, e.g., *Cochliobolus heterostrophus*. In a specific embodiment, the 3' UTR comprises the nucleotide sequence of all or a fragment of the 3' UTR of a *Cochliobolus heterostrophus* gene encoding β-glucosidase.

In a specific embodiment, the 3' UTR comprises the nucleotide sequence of SEQ ID NO:7. Suitable 3' UTRs can comprise a nucleotide sequence having at least 70%, 75%, 80%, 85%, 90%, 95%, 96%, 97%, 98%, or 99% sequence identity to SEQ ID NO:7.

4.2. Methods of Making Expression Cassettes

Techniques for the manipulation of nucleic acids, including techniques for the synthesis, isolation, cloning, detection, and identification are well known in the art and are well described in the scientific and patent literature. See, e.g., Sambrook et al., eds., Molecular Cloning: A Laboratory Manual (2nd Ed.), Vols. 1-3, Cold Spring Harbor Laboratory (1989); Ausubel et al., eds., Current Protocols in Molecular Biology, John Wiley & Sons, Inc., New York (1997); Tijssen, ed., Laboratory Techniques in Biochemistry and Molecular Biology: Hybridization With Nucleic Acid Probes, Part I. Theory and Nucleic Acid Preparation, Elsevier, N.Y. (1993). Nucleic acids comprising the expression cassettes described herein or components thereof include isolated, synthetic, and recombinant nucleic acids.

Expression cassettes and components thereof can readily be made and manipulated from a variety of sources, either by cloning from genomic or complementary DNA, e.g., by using the well known polymerase chain reaction (PCR). See, for example, Innis et al., 1990, PCR Protocols: A Guide to Methods and Application, Academic Press, New York. Expression cassettes and components thereof can also be made by chemical synthesis, as described in, e.g., Adams, 1983, J. Am. Chem. Soc. 105:661; Belousov, 1997, Nucleic Acids Res. 25:3440-3444; Frenkel, 1995, Free Radic. Biol. Med. 19:373-380; Blommers, 1994, Biochemistry 33:7886-7896; Narang, 1979, Meth. Enzymol. 68:90; Brown, 1979, Meth. Enzymol. 68:109; Beaucage, 1981, Tetra. Lett. 22:1859; U.S. Pat. No. 4,458,066.

The promoter, 5' UTR and 3' UTR of an expression cassette of the disclosure be operably linked in a vector. The vector can also include the POI coding sequence, or one or more convenient restriction sites between the 5' UTR and 3' UTR sequences to allow for insertion or substitution of the POI coding sequence. The procedures used to ligate the components described herein to construct the recombinant expression vectors are well known to one skilled in the art (see, e.g., et al., eds., Molecular Cloning: A Laboratory Manual (2nd Ed.), Vols. 1-3, Cold Spring Harbor Laboratory (1989)). As will be described further below, vectors comprising expression cassettes described herein typically contain features making them suitable for introduction into filamentous fungal cells.

4.3. Recombinant Filamentous Fungal Cells

The expression cassettes described herein are usefully expressed in filamentous fungal cells suited to the production of one or more polypeptides of interest. Accordingly, the present disclosure provides recombinant filamentous fungal cells comprising expression cassettes of the disclosure and methods of introducing expression cassettes into filamentous fungal cells.

Suitable filamentous fungal cells include all filamentous forms of the subdivision Eumycotina (see Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungal cell can be from a fungus belonging to any species of *Aspergillus, Trichoderma, Chrysosporium, Cephalosporium, Neurospora, Podospora, Endothia, Cochiobolus, Pyricularia, Rhizomucor, Hansenula, Humicola, Mucor, Tolypocladium, Fusarium, Penicillium, Talaromyces, Emericella, Hypocrea, Acremonium, Aureobasidium, Beauveria, Cephalosporium, Ceriporiopsis, Chaetomium, Paecilomyces, Claviceps, Cryptococcus, Cyathus, Gilocladium, Magnaporthe, Myceliophthora, Myrothecium, Phanerochaete, Paecilomyces, Rhizopus, Schizophylum, Stagonospora, Thermomyces, Thermoascus, Thielavia, Trichophyton, Trametes,* and *Pleurotus*. More preferably, the recombinant cell is a *Trichoderma* sp. (e.g., *Trichoderma reesei*), *Penicillium* sp., *Humicola* sp. (e.g., *Humicola insolens*); *Aspergillus* sp. (e.g., *Aspergillus niger*), *Chrysosporium* sp., *Fusarium* sp., or *Hypocrea* sp. Suitable cells can also include cells of various anamorph and teleomorph forms of these filamentous fungal genera.

Exemplary filamentous fungal species include but are not limited to *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum, Phanerochaete chrysosporium, Phlebia radiate, Pleurotus eryngii, Thielavia terrestris, Trichoderma harzianum, Trichoderma longibrachiatum, Trichoderma reesei,* or *Trichoderma viride*.

Recombinant filamentous fungal cells comprise an expression cassette as described above in Section 4.1. The expression cassette can be extra-genomic or integrated into the cell's genome. FIG. 2A provides a schematic of a recombinant filamentous fungal cell containing an extra-genomic expression cassette. As depicted, the recombinant filamentous fungal cell (5) carrying a vector comprising an expression cassette (6), the expression cassette comprising a promoter (1), a 5' UTR (2), a polypeptide coding sequence (3), and a 3' UTR (4). The expression cassette is not integrated into the chromosome (7) of the recombinant filamentous fungal cell (5). FIG. 2B provides a schematic of a recombinant filamentous fungal cell containing a genomic expression cassette. As depicted the recombinant filamentous fungal cell (5') comprises an expression cassette (6'), which is integrated into the chromosome (7') of the recombinant filamentous fungal cell (5').

The recombinant filamentous fungal cell of FIG. 2B can be generated by introducing and integrating a complete expression cassette into the host chromosome. Alternatively, the recombinant filamentous fungal cell of FIG. 2B may be generated by introducing subset of the components of the expression cassette into the chromosome in such a way and in a location so as to recapitulate a complete expression cassette within the host chromosome. For example, as depicted in FIG. 2C, a vector (8) comprising a promoter (1), a 5' UTR (2), a sequence of a polypeptide coding region homologous to that of a native fungal cell gene (4'), and a sequence homologous to from a region upstream of the native fungal cell gene (9), can be integrated by homologous recombination at a location upstream (on the 5' end) of the native gene comprising a 3' UTR in the chromosome (7') of a filamentous fungal cell to generate a complete expression cassette as depicted in FIG. 2B. In another example, a suitable promoter may be integrated upstream of the 5' UTR of a native gene in the chromosome. Other combinations are also possible, provided that a genomic expression cassette comprising all four components in the results.

Suitable methods for introducing expression cassettes, as well as methods for integrating expression cassettes into the filamentous fungal cell genome are described in further detail below.

4.4. Vectors

The filamentous fungal cells of the present disclosure are engineered to comprise an expression cassette, resulting in recombinant or engineered filamentous fungal cells. Expression cassettes, or components thereof, can be introduced into filamentous fungal cells by way of suitable vectors. The choice of the vector will typically depend on the compatibility of the vector with the into which the vector is to be introduced (e.g., a filamentous fungal cell or a host cell, such as a bacterial cell, useful for propagating or amplifying the vector), whether autonomous replication of the vector inside the filamentous fungal cell and/or integration of the vector into the filamentous fungal cell genome is desired. The vector can be a viral vector, a phage, a phagemid, a cosmid, a fosmid, a bacteriophage, an artificial chromosome, a cloning vector, an expression vector, a shuttle vector, a plasmid (linear or closed circular), or the like. Vectors can include chromosomal, non-chromosomal and synthetic DNA sequences. Large numbers of suitable vectors are known to those of skill in the art, and are commercially available. Low copy number or high copy number vectors may be employed. Examples of suitable expression and integration vectors are provided in Sambrook et al., eds., Molecular Cloning: A Laboratory Manual (2nd Ed.), Vols. 1-3, Cold Spring Harbor Laboratory (1989), and Ausubel et al., eds., Current Protocols in Molecular Biology, John Wiley & Sons, Inc., New York (1997), and van den Hondel et al. (1991) in Bennett and Lasure (Eds.) MORE GENE MANIPULATIONS IN FUNGI, Academic Press pp. 396-428 and U.S. Pat. No. 5,874,276. Reference is also made to the Filamentous Fungal Genetics Stock Center Catalogue of Strains (FGSC, <www.fgsc.net>) for a list of vectors. Particularly useful vectors include vectors obtained from commercial sources, such as Invitrogen and Promega. Specific vectors suitable for use in filamentous fungal cells include vectors such as pFB6, pBR322, pUC18, pUC100, pDON™201, pDONR™221, pENTR™, pGEM®3Z and pGEM®4Z.

For some applications, it may be desirable for the expression cassette, or components thereof, to be maintained as extra-genomic elements. For such applications, suitable vectors comprising an expression cassette or components are preferably capable of autonomously replicating in a cell, independent of chromosomal replication. Accordingly, in some embodiments, the vector comprises an origin of replication enabling it to replicate autonomously in a cell, such as in a filamentous fungal cell.

For many applications, it is desirable to have a tool for selecting recombinant cells containing the vector. Thus, in some embodiments, the vector comprises a selectable marker. A selectable marker is a gene the product of which provides a selectable trait, e.g., antibiotic, biocide or viral resistance, resistance to heavy metals, or prototrophy in auxotrophs. Selectable markers useful in vectors for transformation of various filamentous fungal strains are known in the art. See, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6.; and Kinghorn et al. (1992) APPLIED MOLECULAR GENETICS OF FILAMENTOUS FUNGI, Blackie Academic and Professional, Chapman and Hall, London). Examples of selectable markers which confer antimicrobial resistance include hygromycin and phleomycin. Further exemplary selectable markers include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), pyr4 (orotidine-5'-monophosphate decarboxylase) and trpC (anthranilate synthase). As a specific example, the amdS gene, allows transformed cells to grow on acetamide as a nitrogen source. See, e.g., Kelley et al., 1985, EMBO J. 4:475-479 and Penttila et al., 1987, Gene 61:155-164. Other specific examples of selectable markers include amdS and pyrG genes of *Aspergillus nidulans* or *Aspergillus oryzae* and the bar gene of *Streptomyces hygroscopicus*.

4.5. Methods of Making Recombinant Filamentous Fungal Cells

Recombinant filamentous fungal cells as provided herein, are generated by introducing one or more components of an expression cassette into a suitable filamentous fungal cell. Numerous techniques for introducing nucleic acids into cells, including filamentous fungal cells are known. Nucleic acids may be introduced into the cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)). General transformation techniques are known in the art (See, e.g., Ausubel et al., eds., Current Protocols in Molecular Biology, John Wiley & Sons, Inc., New York (1997); and Sambrook et al., eds., Molecular Cloning: A Laboratory Manual (2nd Ed.), Vols. 1-3, Cold Spring Harbor Laboratory (1989), and Campbell et al., 1989, Curr. Genet. 16:53-56).

Suitable procedures for transformation of various filamentous fungal strains have been described. See e.g., EP 238 023 and Yelton et al, 1984, Proceedings of the National Academy of Sciences USA 81: 1470-1474 for descriptions of transformation in *Aspergillus* host strains. Reference is also made to Cao et al., 2000, Sci. 9:991-1001 and EP 238 023 for transformation of *Aspergillus* strains and WO96/00787 for transformation of *Fusarium* strains. See also, U.S. Pat. Nos. 6,022,725; 6,268,328; Harkki et al., 1991, Enzyme Microb. Technol. 13:227-233; Harkki et al., 1989, Bio Technol. 7:596-603; EP 244,234; EP 215,594; and Nevalainen et al., "The Molecular Biology of *Trichoderma* and its Application to the Expression of Both Homologous and Heterologous Genes", in MOLECULAR INDUSTRIAL MYCOLOGY, Eds. Leong and Berka, Marcel Dekker Inc., NY (1992) pp. 129-148), for transformation of, and heterologous polypeptide expression, in *Trichoderma*.

In many instances, the introduction of an expression vector into a filamentous fungal cell can involve a process consisting of protoplast formation, transformation of the protoplasts, and regeneration of the strain wall according to methods known in the art. See, e.g., U.S. Pat. No. 7,723,079, Campbell et al., 1989, Curr. Genet. 16:53-56, and Examples below.

In some instances, it is desirable to generate a recombinant filamentous fungal cell in which the expression cassette is integrated in the filamentous fungal genome, as described above. Numerous methods of integrating DNA into filamentous fungal chromosomes are known in the art. Integration of a vector, or portion thereof, into the chromosome of a filamentous fungal cell can be carried out by homologous recombination, non-homologous recombination, or transposition. For applications where site-specific integration is desirable, such as when an expression cassette is generated in the fungal cell genome by operably linking components of an expression cassette to a native gene within the fungal cell's chromosome, vectors typically include targeting sequences that are highly homologous to the sequence flanking the desired site of integration, for example as described in Section 4.3. Vectors can include homologous sequence ranging in length from 100 to 1,500 nucleotides, preferably 400 to 1,500 nucleotides, and most preferably 800 to 1,500 nucleotides.

4.6. Use of Recombinant Filamentous Fungal Cells

The recombinant filamentous fungal cells described herein are useful for producing polypeptides of interest. Accordingly, the present disclosure provides methods for producing a polypeptide of interest, comprising culturing a recombinant filamentous fungal cell under conditions that result in expression of the polypeptide of interest. Optionally, the method further comprises additional steps, which can include recovering the polypeptide and purifying the polypeptide.

Suitable filamentous fungal cell culture conditions and culture media are well known in the art. Culture conditions, such as temperature, pH and the like, will be apparent to those skilled in the art. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). Cell culture media in general are set forth in Atlas and Parks (eds.), 1993, The Handbook of Microbiological Media, CRC Press, Boca Raton, Fla., which is incorporated herein by reference. For recombinant expression in filamentous fungal cells, the cells are cultured in a standard medium containing physiological salts and nutrients, such as described in Pourquie et al., 1988, Biochemistry and Genetics of Cellulose Degradation, Aubert et al., eds., Academic Press, pp. 71-86; and Ilmen et al., 1997, Appl. Environ. Microbiol. 63:1298-1306. Culture conditions are also standard, e.g., cultures are incubated at 28° C. in shaker cultures or fermentors until desired levels of polypeptide expression are achieved. Where an inducible promoter is used, the inducing agent, e.g., a sugar, metal salt or antibiotics, is added to the medium at a concentration effective to induce polypeptide expression.

Recombinant filamentous fungal cells may be cultured by shake flask cultivation, small-scale or large-scale fermentation (including continuous, batch, fed-batch, or solid state fermentations) in laboratory or industrial fermentors performed in a suitable medium and under conditions allowing the polypeptide of interest to be expressed and/or isolated.

Techniques for recovering and purifying expressed protein are well known in the art and can be tailored to the particular polypeptide(s) being expressed by the recombinant filamentous fungal cell. Polypeptides can be recovered from the culture medium and or cell lysates. In embodiments where the method is directed to producing a secreted polypeptide, the polypeptide can be recovered from the culture medium. Polypeptides may be recovered or purified from culture media by a variety of procedures known in the art including but not limited to, centrifugation, filtration, extraction, spray-drying, evaporation, or precipitation. The recovered polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989).

The recombinant filamentous fungal cells of the disclosure can be used in the production of cellulase compositions. The cellulase compositions of the disclosure typically include a recombinantly expressed POI, which is preferably a cellulase, a hemicellulase or an accessory polypeptide. Cellulase compositions typically include one or more cellobiohydrolases and/or endoglucanases and/or one or more β-glucosidases, and optionally include one or more hemicellulases and/or accessory proteins. In their crudest form, cellulase compositions contain the culture of the recombinant cells that produced the enzyme components. "Cellulase compositions" also refers to a crude fermentation product of the filamentous fungal cells that recombinantly express one or more of a cellulase, hemicellulase and/or accessory protein. A crude fermentation is preferably a fermentation broth that has been separated from the filamentous fungal cells and/or cellular debris (e.g., by centrifugation and/or filtration). In some cases, the enzymes in the broth can be optionally diluted, concentrated, partially purified or purified and/or dried. The recombinant POI produced by the recombinant filamentous fungal cells of the disclosure can be co-expressed with one or more of the other components of the cellulase composition (optionally recombinantly expressed using the same or a different expression cassette of the disclosure) or it can be expressed separately, optionally purified and combined with a composition comprising one or more of the other cellulase components.

Cellulase compositions comprising one or more POIs produced by the recombinant filamentous fungal cells of the disclosure can be used in saccharification reaction to produce simple sugars for fermentation. Accordingly, the present disclosure provides methods for saccharification comprising contacting biomass with a cellulase composition comprising a POI of the disclosure and, optionally, subjecting the resulting sugars to fermentation by a microorganism.

The term "biomass," as used herein, refers to any composition comprising cellulose (optionally also hemicellulose and/or lignin). As used herein, biomass includes, without limitation, seeds, grains, tubers, plant waste or byproducts of food processing or industrial processing (e.g., stalks), corn (including, e.g., cobs, stover, and the like), grasses (including, e.g., Indian grass, such as *Sorghastrum nutans*; or, switchgrass, e.g., *Panicum* species, such as *Panicum virgatum*), wood (including, e.g., wood chips, processing waste), paper, pulp, and recycled paper (including, e.g., newspaper, printer paper, and the like). Other biomass materials include, without limitation, potatoes, soybean (e.g., rapeseed), barley, rye, oats, wheat, beets, and sugar cane bagasse.

The saccharified biomass (e.g., lignocellulosic material processed by cellulase compositions of the disclosure) can be made into a number of bio-based products, via processes such as, e.g., microbial fermentation and/or chemical synthesis. As used herein, "microbial fermentation" refers to a process of growing and harvesting fermenting microorganisms under suitable conditions. The fermenting microorganism can be any microorganism suitable for use in a desired fermentation process for the production of bio-based products. Suitable fermenting microorganisms include, without limitation, filamentous fungi, yeast, and bacteria. The saccharified biomass can, for example, be made it into a fuel (e.g., a biofuel such as a bioethanol, biobutanol, biomethanol, a biopropanol, a biodiesel, a jet fuel, or the like) via fermentation and/or chemical synthesis. The saccharified biomass can, for example, also be made into a commodity chemical (e.g., ascorbic acid, isoprene, 1,3-propanediol), lipids, amino acids, polypeptides, and enzymes, via fermentation and/or chemical synthesis.

Thus, in certain aspects, POIs expressed by the recombinant filamentous fungal cells of the disclosure find utility in the generation of ethanol from biomass in either separate or simultaneous saccharification and fermentation processes. Separate saccharification and fermentation is a process whereby cellulose present in biomass is saccharified into simple sugars (e.g., glucose) and the simple sugars subsequently fermented by microorganisms (e.g., yeast) into ethanol. Simultaneous saccharification and fermentation is a process whereby cellulose present in biomass is saccharified into simple sugars (e.g., glucose) and, at the same time and in the same reactor, microorganisms (e.g., yeast) ferment the simple sugars into ethanol.

Prior to saccharification, biomass is preferably subject to one or more pretreatment step(s) in order to render cellulose material more accessible or susceptible to enzymes and thus more amenable to hydrolysis by POI polypeptides of the disclosure.

In an exemplary embodiment, the pretreatment entails subjecting biomass material to a catalyst comprising a dilute solution of a strong acid and a metal salt in a reactor. The biomass material can, e.g., be a raw material or a dried material. This pretreatment can lower the activation energy, or the temperature, of cellulose hydrolysis, ultimately allowing higher yields of fermentable sugars. See, e.g., U.S. Pat. Nos. 6,660,506; 6,423,145.

Another exemplary pretreatment method entails hydrolyzing biomass by subjecting the biomass material to a first hydrolysis step in an aqueous medium at a temperature and a pressure chosen to effectuate primarily depolymerization of hemicellulose without achieving significant depolymerization of cellulose into glucose. This step yields a slurry in which the liquid aqueous phase contains dissolved monosaccharides resulting from depolymerization of hemicellulose, and a solid phase containing cellulose and lignin. The slurry is then subject to a second hydrolysis step under conditions that allow a major portion of the cellulose to be depolymerized, yielding a liquid aqueous phase containing dissolved/soluble depolymerization products of cellulose. See, e.g., U.S. Pat. No. 5,536,325.

A further exemplary method involves processing a biomass material by one or more stages of dilute acid hydrolysis using about 0.4% to about 2% of a strong acid; followed by treating the unreacted solid lignocellulosic component of the acid hydrolyzed material with alkaline delignification. See, e.g., U.S. Pat. No. 6,409,841. Another exemplary pretreatment method comprises prehydrolyzing biomass (e.g., lignocellulosic materials) in a prehydrolysis reactor; adding an acidic liquid to the solid lignocellulosic material to make a mixture; heating the mixture to reaction temperature; maintaining reaction temperature for a period of time sufficient to fractionate the lignocellulosic material into a solubilized portion containing at least about 20% of the lignin from the lignocellulosic material, and a solid fraction containing cellulose; separating the solubilized portion from the solid fraction, and removing the solubilized portion while at or near reaction temperature; and recovering the solubilized portion. The cellulose in the solid fraction is rendered more amenable to enzymatic digestion. See, e.g., U.S. Pat. No. 5,705,369. Further pretreatment methods can involve the use of hydrogen peroxide $H_2O_2$. See Gould, 1984, Biotech, and Bioengr. 26:46-52.

Pretreatment can also comprise contacting a biomass material with stoichiometric amounts of sodium hydroxide and ammonium hydroxide at a very low concentration. See Teixeira et al., 1999, Appl. Biochem. and Biotech. 77-79:19-34. Pretreatment can also comprise contacting a lignocellulose with a chemical (e.g., a base, such as sodium carbonate or potassium hydroxide) at a pH of about 9 to about 14 at moderate temperature, pressure, and pH. See PCT Publication WO2004/081185.

Ammonia pretreatment can also be used. Such a pretreatment method comprises subjecting a biomass material to low ammonia concentration under conditions of high solids. See, e.g., U.S. Patent Publication No. 20070031918 and PCT publication WO 06/110901.

Table 1 below provides a list of the SEQ ID NOs referenced herein and the corresponding polynucleotide or polypeptide sequences.

TABLE 1

| SEQ ID NO: | Description | Sequence |
|---|---|---|
| 1 | CaMV 35S promoter | GTCAAAGATT CAAATAGAGG ACCTAACAGA ACTCGCCGTA AAGACTGGCG AACAGTTCAT ACAGAGTCTC TTACGACTCA ATGACAAGAA GAAATCTTC GTCAACATGG TGGAGCACGA CACACTTGTC TACTCCAAAA ATATCAAAGA TACAGTCTCA GAAGACCAAA GGGCAATTGA GACTTTTCAA CAAAGGGTAA TATCCGGAAA CCTCCTCGGA TTCCATTGCC CAGCTATCTG TCACTTTATT GTGAAGATAG TGGAAAAGGA AGGTGGCTCC TACAAATGCC ATCATTGCGA TAAAGGAAAG GCCATCGTTG AAGATGCCTC TGCCGACAGT GGTCCCAAAG ATGGACCCCC ACCCACGAGG AGCATCGTGG AAAAAGAAGA CGTTCCAACC ACGTCTTCAA AGCAAGTGGA TTGATGTGAT ATCTCCACTG ACGTAAGGGA TGACGCACAA TCCCACTATC CTTCGCAAGA CCCTTCCTCT ATATAAGGAA GTTCATTTCA TTTGGAGAGA ACACG |

TABLE 1-continued

| SEQ ID NO: | Description | Sequence |
|---|---|---|
| 2 | CoYMV promoter | GTGCAACCAC TCAGACAAAA GATGGCACCA ACAGGAGACA AGAGAATGAA TCCAGAAACA TGGAAGATGG TAAGACAGAT AAAAGAAAAG GTGAAAAATC TCCCTGATCT TCAGTTACCA CCTAAAGATT CATTCATCAT AATAGAGACG GATGGTTGTA TGACTGGCTG GGGAGCCGTC TGCAAATGGA AAATGTCAAA GCATGATCCA AGAAGCACCG AAAGAATTTG TGCCTATGCT AGTGGATCAT TCAATCCAAT AAAATCAACC ATCGATGCAG AGATTCAGGC GGCAATCCAT GGCCTGGATA AATTCAAAAT TTATTATCTT GATAAAAAGG AGCTCATAAT TCGCTCAGAC TGTGAAGCAA TTATCAAATT TTACAACAAG ACGAACGAAA ATAAGCCGTC TAGAGTTAGA TGGTTAACAT TTTCAGATTT CTTAACAGGT CTTGGAATCA CAGTTACATT CGAGCACATA GATGGAAAGC ATAATGGCTT AGCAGATGCT CTATCAAGAA TGATAAATTT CATTGTGGAG AAAAATGATG AATCTCCATA CAGGTTCACT TCATCAGTAG AGGACGACCT AAAGGTCTGC AATGATGATC ACGGAAGAAA TTTGATATCC GCCGTCATCA ATGACATCAT CACAGTACTG AGGAGATGAA TACTTAGCCA TGAAGTAGCG TGCGAATATT ACCTATGCCT TTATTCGCAG CGTTAGTGGC ACTGAAAGGC ATAAAGTTTG TTCGTTCTTA TCAAAAACGA ATCTTATCTT TGTAACTTGG TTACCCGGTA TGCCGGTTCC CAAGCTTTAT TTCCTTATTT AAGCACTTGT GTAGTAGCTT AGAAAACCAA CACAACAACA CCAAGAATAC TTTGAGTGTA GTAATTGGTT CTA |
| 3 | CaMV native S1 5' UTR | GTACCGCTGA ATCACCAAT CTCTCTCTAC AAATCTATCT CTCTCTATTT CTC |
| 4 | T. reesei gpd 5' UTR 100 nt fragment | CCTCCTCCCT CTCTCCCTCT CGTTTCTTCC TAACAAACAA CCACCACCAA AATCTCTTTG GAAGCTCACG ACTCACGCAA GCTCAATTCG CAGATACAAA |
| 5 | T. reesei gpd 5' UTR 150 nt fragment | AGCTACCCCG CCAGACTCTC CTGCGTCACC AATTTTTTTC CCTATTTACC CCTCCTCCCT CTCTCCCTCT CGTTTCTTCC TAACAAACAA CCACCACCAA AATCTCTTTG GAAGCTCACG ACTCACGCAA GCTCAATTCG CAGATACAAA |
| 6 | T. reesei gpd 5' UTR 200 nt fragment | ACGATGCGGC TTCTGTTCGC CTGCCCCTCC TCCCACTCGT GCCCTTGACG AGCTACCCCG CCAGACTCTC CTGCGTCACC AATTTTTTTC CCTATTTACC CCTCCTCCCT CTCTCCCTCT CGTTTCTTCC TAACAAACAA CCACCACCAA AATCTCTTTG GAAGCTCACG ACTCACGCAA GCTCAATTCG CAGATACAAA |
| 7 | T. reesei CBH1 terminator | GGCCAGGTCC TGACCCTTA CTACTCTCAG TGCCTGTAAA GCTCCGTGGC GAAAGCCTGA CGCACCGGTA GATTCTTGGT GAGCCCGTAT CATGACGGCG GCGGGAGCTA CATGGCCCCG GGTGATTTAT TTTTTTTGTA TCTACTTCTG ACCCTTTTCA AATATACGGT CAACTCATCT TTCACTGGAG ATGCGGCCTG CTTGGTATTG CGATGTTGTC AGCTTGGCAA ATTGTGGCTT TCGAAAACAC AAAACGATTC CTTAGTAGCC ATGCATTTTA AGATAACGGA ATAGAAGAAA GAGGAAATTA AAAAAAAAA AAACAAACA TCCCGTTCAT AACCCGTAGA ATCGCCGCTC TTCGTGTATC CCAGTACCAC GGCAAAGGTA TTTCATGATC GTTCAATGTT GATATTGTTC CCGCCAGTAT GGCTCCACCC CCATCTCCGC GAATCTCCTC TTCTCGAACG CGGTAGTGGC GCGCCAATTG GTAATGACCC ATAGGGAGAC AAACAGCATA ATAGCAACAG TGGAAATTAG TGGCGCAATA ATTGAGAACA CAGTGAGACC ATAGCTGCG GCCTGGAAAG CACTGTTGGA GACCAACTTG TCCGTTGCGA GGCCAACTTG CATTGCTGTC AGGACGATGA CAACGTAGCG GAGGACCGTC ACAAGGGACG CAAGTGCG |
| 8 | CaMV 35S promoter forward primer | CACCA<u>TTAAT TAA</u>GTCAAAG ATTCAAATAG AGGACCTAAC |
| 9 | CaMV 35S promoter reverse primer | CACCA<u>CGGAC CGT</u><u>ACTAGT</u>C GTGTTCTCTC CAAATGAAAT GA |
| 10 | β-glucosidase forward primer | CACCA<u>ACTAG T</u>ATGCTGTGG CTTGCACAAG CATTGTTGG |
| 11 | β-glucosidase reverse primer | CACCA<u>GGCCG GCC</u>TTATCTA AAGCTGCTAG TGTCCAGTGG GG |
| 12 | CoYMV promoter forward primer | CACCA<u>TTAAT TAA</u>GTGCAAC CACTCAGACA AAAGATGG |
| 13 | CoYMV promoter reverse primer | CACCA<u>CGGAC CGT</u><u>ACTAGT</u>T AGAACCAATT ACTACACTCA AAGTATTC |
| 14 | TR-CBH1t-3' primer | ACTTTGCGTC CCTTGTGACG G |
| 15 | TR-PYR4-5' primer | TTGCATTGGT ACAGCTGCAG G |
| 16 | 5' UTR forward primer -34 from ATG start | GACTCACGCA AGCTCAATTC G |

TABLE 1-continued

| SEQ ID NO: | Description | Sequence |
|---|---|---|
| 17 | 5' UTR forward primer, -140 from ATG start | CCAGACTCTC CTGCGTCACC AAT |
| 18 | 5' UTR forward primer, -229 from ATG start | CTACAATCAT CACCACGATG CTCC |
| 19 | 5' UTR forward primer, -284 from ATG start | CGACATTCTC TCCTAATCAC CAGC |
| 20 | 5' UTR forward primer, -402 from ATG start | GCCGTGCCTA CCTGCTTTAG TATT |
| 21 | 5' UTR forward primer, -443 from ATG start | CCACTATCTC AGGTAACCAG TAC |
| 22 | Reverse primer, +269 from ATG start | GTCTCGCTCC ACTTGATGTT GGCA |
| 23 | pCa forward primer with PacI site | CACCATTAAT TAAGTCAAAG ATTCAAATAG AGGACCTAAC A |
| 24 | CaMV native S1 5' UTR reverse primer | TGTAGAGAGA GATTGGTGAT TTCAGCGGTA CCGTGTTCTC TCCAAATGAA ATGAA |
| 25 | pCaMV S1 5' UTR reverse primer | CACCAACTAG TGAGAAATAG AGAGAGATAG ATTTGTAGAG AGAGATTGGT GATTTCAGC |
| 26 | pCa overlap-100 bp gpd 5' UTR reverse primer | AGAGGGAGAG AGGGAGGAGG CGTGTTCTCT CCAAATGAAA TG |
| 27 | pCa overlap-150 bp gpd 5' UTR reverse primer | GAGAGTCTGG CGGGGTAGCT CGTGTTCTCT CCAAATGAAA TG |
| 28 | pCa overlap-200 bp gpd 5' UTR reverse primer | GCGAACAGAA GCCGCATCGT CGTGTTCTCT CCAAATGAAA TG |
| 29 | pCa overlap-100 bp gpd 5' UTR forward | CATTTCATTT GGAGAGAACA CGCCTCCTCC CTCTCTCCCT CT |
| 30 | pCa overlap-150 bp gpd 5' UTR forward | CATTTCATTT GGAGAGAACA CGAGCTACCC CGCCAGACTC TC |
| 31 | pCa overlap-200 bp gpd 5' UTR forward | CATTTCATTT GGAGAGAACA CGACGATGCG GCTTCTGTTC GC |
| 32 | pWG-SpeI site reverse primer | CACCAACTAG TTTTGTATCT GCGAATTGAG CTTGCGTGA |
| 33 | *Cochliobolus heterostrophus* β-glucosidase nucleotide sequence | ATGCTGTGGC TTGCACAAGC ATTGTTGGTC GGCCTTGCCC AGGCATCGCC CAGGTTCCCT CGTGCTACCA ACGACACCGG CAGTGATTCT TTGAACAATG CCCAGAGCCC GCCATTCTAC CCAAGTCCTT GGGTAGATCC CACCACCAAG GACTGGGCGG CTGCCTATGA AAAAGCAAAG GCTTTTGTTA GCCAATTGAC TCTTATTGAG AAGGTCAACC TCACCACCGG CACTGGATGG CAGAGCGACC ACTGCGTTGG TAACGTGGGC GCTATTCCTC GCCTTGGCTT TGATCCCCTC TGCCTCCAGG ACAGCCCTCT CGGCATCCGT TTCGCAGACT ACGTTTCTGC TTTCCCAGCA GGTGGCACCA TTGCTGCATC ATGGGACCGC TATGAGTTTT ACACCCGCGG TAACGAGATG GGTAAGGAGC ACCGAAGGAA GGGAGTCGAC GTTCAGCTTG GTCCTGCCAT TGGACCTCTT GGTCGCCACC CCAAGGGCGG TCGTAACTGG GAAGGCTTCA GTCCTGATCC TGTACTTTCC GGTGTGGCCG TGAGCGAAAC AGTCCGCGGT ATCCAGGATG CTGGTGTCAT TGCCTGCACT AAGCACTTCC TTCTGAACGA GCAAGAACAT TTCCGTCAGC CCGGCAGTTT CGGAGATATC CCCTTTGTCG ATGCCATCAG CTCCAATACC GATGACACGA CTCTACACGA GCTCTACCTG TGGCCCTTTG CCGACGCCGT CCGCGCTGGT ACTGGTGCCA TCATGTGCTC TTACAACAAG GCCAACAACT CGCAACTCTG CCAAAACTCG CACCTTCAAA ACTATATTCT CAAGGGCGAG CTTGGCTTCC AGGGTTTCAT TGTATCTGAC TGGGATGCAC AGCACTCGGG CGTTGCGTCG GCTTATGCTG GATTGGACAT GACTATGCCT GGTGATACTG GATTCAACAC TGGACTGTCC TTCTGGGGCG CTAACATGAC CGTCTCCATT CTCAACGGCA CCATTCCCCA GTGGCGTCTC GACGATGCGG CCATCCGTAT CATGACCGCA TACTACTTTG TCGGCCTTGA TGAGTCTATC CCTGTCAACT TTGACAGCTG GCAAACTAGC ACGTACGGAT TCGAGCATTT TTTCGGAAAG AAGGGCTTCG |

TABLE 1-continued

| SEQ ID NO: | Description | Sequence |
|---|---|---|
| | | GTCTGATCAA CAAGCACATT GACGTTCGCG AGGAGCACTT CCGCTCCATC<br>CGCCGCTCTG CTGCCAAGTC AACCGTTCTC CTCAAGAACT CTGGCGTCCT<br>TCCCCTCTCT GGAAAGGAGA AGTGGACTGC TGTATTTGGA GAAGATGCTG<br>GCGAAAACCC GCTGGGCCCC AACGGATGCG CTGACCGCGG CTGCGACTCT<br>GGCACCTTGG CCATGGGCTG GGGTTCGGGA ACTGCAGACT TCCCTTACCT<br>CGTCACTCCT CTCGAAGCCA TCAAGCGTGA GGTTGGCGAG AATGGCGGCG<br>TGATCACTTC GGTCACAGAC AACTACGCCA CTTCGCAGAT CCAGACCATG<br>GCCAGCAGGG CCAGCCACTC GATTGTCTTC GTCAATGCCG ACTCTGGTGA<br>AGGTTACATC ACTGTTGATA ACAACATGGG TGACCGCAAC AACATGACTG<br>TGTGGGGCAA TGGTGATGTG CTTGTCAAGA ATATCTCTGC TCTGTGCAAC<br>AACACGATTG TGGTTATCCA CTCTGTCGGC CCAGTCATTA TTGACGCCTG<br>GAAGGCCAAC GACAACGTGA CTGCCATTCT CTGGGCTGGT CTTCCTGGCC<br>AGGAGTCTGG TAACTCGATT GCTGACATTC TATACGGACA CCACAACCCT<br>GGTGGCAAGC TCCCCTTCAC CATTGGCAGC TCTTCAGAGG AGTATGGCCC<br>TGATGTCATC TACGAGCCCA CGAACGGCAT CCTCAGCCCT CAGGCCAACT<br>TTGAAGAGGG CGTCTTCATT GACTACCGCG CGTTTGACAA GGCGGGCATT<br>GAGCCCACGT ACGAATTTGG CTTTGGTCTT TCGTACACGA CTTTTGAATA<br>CTCGGACCTC AAGGTCACTG CGCAGTCTGC CGAGGCTTAC AAGCCTTTCA<br>CCGGCCAGAC TTCGGCTGCC CCTACATTCG GAAACTTCAG CAAGAACCCC<br>GAGGACTACC AGTACCCTCC CGGCCTTGTT TACCCCGACA CGTTCATCTA<br>CCCCTACCTC AACTCGACTG ACCTCAAGAC GGCATCTCAG GATCCCGAGT<br>ACGGCCTCAA CGTTACCTGG CCCAAGGGCT CTACCGATGG CTCGCCTCAG<br>ACCCGCATTG CGGCTGGTGG TGCGCCCGGC GGTAACCCCC AGCTCTGGGA<br>CGTTTTGTTC AAGGTCGAGG CCACGATCAC CAACACTGGT CACGTTGCTG<br>GTGACGAGGT GGCCCAGGCG TACATCTCGC TTGGTGGCCC CAACGACCCC<br>AAGGTGCTAC TCCGTGACTT TGACCGCTTG ACCATCAAGC CTGGTGAGAG<br>CGCTGTTTTC ACAGCCAACA TCACCCGCCG TGATGTCAGC AACTGGGACA<br>CTGTCAGCCA GAACTGGGTC ATTACCGAGT ACCCCAAGAC GATCCACGTT<br>GGTGCCAGTT CGAGGAACCT TCCTCTTTCT GCCCCACTGG ACACTAGCAG<br>CTTTAGATAA |
| 34 | Cochliobolus heterostrophus β-glucosidase polypeptide sequence | MLWLAQALLV GLAQASPRFP RATNDTGSDS LNNAQSPPFY PSPWVDPTTK<br>DWAAAYEKAK AFVSQLTLIE KVNLTTGTGW QSDHCVGNVG AIPRLGFDPL<br>CLQDSPLGIR FADYVSAFPA GGTIAASWDR YEFYTRGNEM GKEHRRKGVD<br>VQLGPAIGPL GRHPKGGRNW EGFSPDPVLS GVAVSETVRG IQDAGVIACT<br>KHFLLNEQEH FRQPGSFGDI PFVDAISSNT DDTTLHELYL WPFADAVRAG<br>TGAIMCSYNK ANNSQLCQNS HLQNYILKGE LGFQGFIVSD WDAQHSGVAS<br>AYAGLDMTMP GDTGFNTGLS FWGANMTVSI LNGTIPQWRL DDAAIRIMTA<br>YYFVGLDESI PVNFDSWQTS TYGFEHFFGK KGFGLINKHI DVREEHFRSI<br>RRSAAKSTVL LKNSGVLPLS GKEKWTAVFG EDAGENPLGP NGCADRGCDS<br>GTLAMGWGSG TADFPYLVTP LEAIKREVGE NGGVITSVTD NYATSQIQTM<br>ASRASHSIVF VNADSGEGYI TVDNNMGDRN NMTVWGNGDV LVKNISALCN<br>NTIVVIHSVG PVIIDAWKAN DNVTAILWAG LPGQESGNSI ADILYGHHNP<br>GGKLPFTIGS SSEEYGPDVI YEPTNGILSP QANFEEGVFI DYRAFDKAGI<br>EPTYEFGFGL SYTTFEYSDL KVTAQSAEAY KPFTGQTSAA PTFGNFSKNP<br>EDYQYPPGLV YPDTFIYPYL NSTDLKTASQ DPEYGLNVTW PKGSTDGSPQ<br>TRIAAGGAPG NPQLWDVLFK VEATITNTGH VAGDEVAQAY ISLGGPNDPK<br>VLLRDFDRLT IKPGESAVFT ANITRRDVSN WDTVSQNWVI TEYPKTIHVG<br>ASSRNLPLSA PLDTSSFR |

5. EXAMPLES

5.1. Example 1

Construction of a Vector Containing a CaMV Promoter Sequence and the Coding Sequence for *Cochliobolus Heterostrophus* β-glucosidase This example describes the construction of an expression vector comprising a cauliflower mosaic virus (CaMV) 35S promoter operably linked in a 5' to 3' direction to a sequence coding for *Cochliobolus heterostrophus* β-glucosidase and a terminator sequence from *T. reesei* CBHI, which includes a 3' UTR.

Construction of Plasmids Containing CaMV 35S Promoter.

First, vectors containing a cauliflower mosaic virus (CaMV) 35S promoter were constructed by inserting the viral CaMV 35S promoter into plasmid pW, which consists of the commercial plasmid pBluescript II SK (+), the *Trichoderma reesei* selectible marker PYR4 (encoding orotidine-5'-monophosphate decarboxylase) and the terminator from CBHI (encoding exo-cellobiohydrolase I). All procedures utilizing commercial vendor products, described in this and the following Examples, were carried out by following the instructions of the manufacturer. The vector containing CaMV 35S promoter is denominated pCa. The promoter was cloned into the plasmid using conventional techniques. The promoter was amplified by polymerase chain reaction (PCR) from a synthesized template with AccuPrime™ Pfx SuperMix (Invitrogen, Carlsbad, Calif.) using the primers listed below.

TABLE 2

| SEQ ID NO: | Description | Sequence |
|---|---|---|
| 8 | CaMV 35S forward (5') primer | CACCA<u>TTAATTAA</u>GTCAAAGATTCAAATAGAGGACCTAAC |
| 9 | CaMV 35S reverse (3') primer | CACCA<u>CGGACCG</u>T<u>ACTAGT</u>CGTGTTCTCTCCAAATGAAATGA |

Each primer contains a CACCA sequence of nucleotides on its 5' end to ensure efficient cutting. The forward primer contains a PacI restriction site and the reverse primer contains an RsrII restriction site as well as a SpeI restriction site. In the table above, restriction sites are underlined. The amplified promoter was then purified with the DNA Clean & Concentrator™-5 kit (Zymo Research, Irvine, Calif.), digested with PacI and SpeI (NEB, Ipswich, Mass.); gel purified with Zymoclean™ Gel DNA Recovery Kit (Zymo Research, Irvine, Calif.) to prepare the promoter DNA for ligation. Plasmid DNA was prepared by digesting pW with PacI and SpeI at 37° C. for 2 hours and then purified with the DNA Clean & Concentrator™ 5 kit. The ligation reaction between the promoter DNA and the plasmid DNA was carried with T4 DNA Ligase (NEB, Ipswich, Mass.). Each 10 μL ligation consisted of 50 ng of plasmid DNA, 20 ng or 40 ng of promoter DNA (so that promoter to vector molar ratio is 5:1), 1×T4 DNA Ligase buffer and 0.20-T4 DNA ligase. The sequence of the inserted promoter was verified by sequencing using Big-Dye™ terminator chemistry (Applied Biosystems, Inc., Foster City, Calif.). FIG. 3A depicts a schematic map of the resulting pCa vector.

Construction of vector containing a *Cochliobolus heterostrophus* β-glucosidase coding sequence. The pCa vector was digested with SpeI and FseI at 37° C. for 2 hours and purified with the DNA Clean & Concentrator™ 5 kit. Sequences encoding a β-glucosidase were amplified using AccuPrime™ Pfx SuperMix with the primers listed below.

TABLE 3

| SEQ ID NO: | Description | Sequence |
|---|---|---|
| 10 | β-glucosidase forward (5') primer | CACCA<u>ACTAGT</u>*ATGCTGTGGCTTGCACAAGCATTGTTGG* |
| 11 | β-glucosidase reverse (3') primer | CACCA<u>GGCCGGCC</u>*TTATCTAAAGCTGCTAGTGTCCAGTGGGG* |

Primers were designed to have a melting temperature ($T_M$) of 60° C., a CACCA sequence on their 5' end to ensure efficient cutting in subsequent steps. The forward primer then included a SpeI restriction site and the reverse primer an FseI restriction site to allow for cloning into the pCa vector. Restriction sites are underlined and the sequence corresponding to the β-glucosidase coding sequence is shown in italics in the table above. The amplified coding sequence was then purified with the DNA Clean & Concentrator™ 5 (Zymo Research, Irvine, Calif.) digested with PacI and SpeI (NEB, Ipswich, Mass.); gel purified with Zymoclean™ Gel DNA Recovery Kit (Zymo Research, Irvine, Calif.) to prepare the coding sequence DNA for ligation. Ligation was carried out using T4 DNA Ligase (NEB, Ipswich, Mass.). Each 10 μL ligation consisted of 50 ng of pCa vector, 20 ng or 40 ng of coding sequence DNA (so that coding sequence to pCa vector molar ratio is 5:1), 1×T4 DNA Ligase buffer and 0.2 μL T4 DNA Ligase. The nucleotide sequences of the final constructs were confirmed using Big-Dye™ terminator chemistry (Applied Biosystems, Inc., Foster City, Calif.). The plasmid containing the CaMV 35S promoter operably linked to β-glucosidase is denominated pCa-BG.

5.2. Example 2

Construction of a Vector Containing a CoYMV Promoter Sequence and the Coding Sequence for *Cochliobolus Heterostrophus* β-Glucosidase This example describes the construction of an expression vector comprising a Commelina yellow mottle virus (CoYMV) promoter operably linked in a 5' to 3' direction to a protein coding sequence for *Cochliobolus* heterostrophus β-glucosidase. Expression vectors comprising the CoYMV promoter and *Cochliobolus heterostrophus* β-glucosidase were constructed as described above in Example 1, except that a CoYMV promoter instead of a CaMV 35S promoter was subcloned into the pW plasmid, using appropriate primers. The plasmid containing the CoYMV promoter is denominated pCoY and was constructed using the following primers: the forward primer for CoYMV was CACCA TTAATTAAGTGCAACCACTCAGACAAAAGATGG (SEQ ID NO:12) and the reverse primer for CoYMC was CACCA CGGACCGTACTAGTT AGAACCAATT ACTACACTCAAAGTATTC (SEQ ID NO:13). FIG. 3B depicts a schematic map of the resulting pCoY vector. The plasmid containing the CoYMV promoter operably linked to β-glucosidase is denominated pCoY-BG.

5.3. Example 3

Transformation of *Trichoderma Reesei* with Vectors Containing CaMV or CoYMV Promoters and a Protein Coding Sequence This example describes the introduction of an expression vector comprising either CaMV 35S promoter or CoYMV promoter operably linked in a 5' to 3' direction to a protein coding sequence for *Cochliobolus heterostrophus* β-glucosidase.

Media. The following media was used for the transformation procedure. *Aspergillus* Complete Medium (ACM) was made as follows: 10 g/l yeast extract (1% final); 25 g/l glucose (2.5% final); 10 g/l Bacto Peptone (Bacto Laboratories, Liverpool, NSW, Australia) (1% final); 7 mM KCl; 11 mM $KH_2PO_4$; 2 mM $MgSO_4$; 77 μM $ZnSO_4$; 178 μM $H_3BO_3$; 25 μM $MnCl_2$; 18 μM $FeSO_4$; 7.1 μM $CoCl_2$; 6.4 μM $CuSO_4$; 6.2 μM $Na_2MoO_4$; 134 μM $Na_2EDTA$; 1 mg/ml riboflavin; 1 mg/ml thiamine; 1 mg/ml nicotinamide; 0.5 mg/ml pyridoxine; 0.1 mg/ml pantothenic acid; 2 μg/ml biotin. *Trichoderma* Minimal Medium (TMM) plates were made as follows: 10 g/l glucose; 45 mM $(NH_4)_2SO_4$; 73 mM $KH_2PO_4$; 4 mM $MgSO_4$; 10 mM trisodium citrate; 18 μM $FeSO_4$; 10 μM $MnSO_4$; 5 μM $ZnSO_4$; 14 μM $CaCl_2$; 15 g/l agar (TMM overlay contains 7.5 g/l agar).

Amplification of pCa-BG or pCoY-BG DNA. The amplification reactions (50 μl) were set up to contain 1×AccuPrime Pfx Supermix (Invitrogen, Carlsbad, Calif.), 0.28 μM primer TR-CBHIt-3' (ACTTTGCGTCCCTTGTGACGG) (SEQ ID NO:14), 0.28 μM primer TR-PYR4-5' (TTGCATTGGTACAGCTGCAGG) (SEQ ID NO:15), and 30-40 ng of pCa-BG or pCoY-BG DNA. The reactions were subjected to thermocyling in a GeneAmp 9700 (Applied Biosystems, Carlsbad, Calif.) programmed as follows: 95° C. for 3 minutes, then 30 cycles each of 45 seconds at 95° C., 45 seconds at 57° C., and 8 5 minutes at 68° C. (with a 10 minute final extension at 68° C.). The reaction products were visualized on a ReadyAgrose gel (Bio-Rad, Hercules, Calif.) and purified using a QIAquick PCR purification kit (Qiagen, Valencia, Calif.) according to the manufacturer's instructions.

Transformation of *Trichoderma Reesei*. A pyr-4-deficient mutant of *Trichoderma reesei* strain MCG80 was used as the expression host for the pCa-BG or pCoY-BG constructs, allowing for pyr4 selection of transformants. Mycelial cultures of MCG80pyr4 were produced by adding $2.2 \times 10^8$ conidia to 400 ml ACM medium and incubating in an orbital shaking incubator at 30° C. and 275 rpm for 18 hrs. Mycelia were gently washed with 450 ml of KM (0.7 M KCl; 20 mM MES buffer, pH 6.0) using a sterile 1-liter filter unit. Washed mycelia were suspended in 100 ml of KM containing 15 mg/ml Lysing Enzymes from *Trichoderma harzianum* (Sigm-Aldrich, St. Louis, Mo.) and incubated in an orbital shaker at 30° C. and 60 rpm for 90 minutes. Mycelial debris was removed from the protoplast suspension by filtering through Miracloth (EMD Biosciences, Gibbstown, N.J.). The resulting suspension was transferred to a 250 ml centrifuge bottle and filled to the top with ice cold STC (1 M sorbitol; 50 mM $CaCl_2$; 10 mM Tris-HCl, pH 7.5), mixed and centrifuged (15 min, 2100×g, 4° C.). After discarding the supernatant, the pellet was gently suspended in 250 ml ice cold STC and centrifuged again (15 min, 2100×g, 4° C.). The resulting pellet was suspended in STC at a concentration of approximately $5 \times 10^7$ protoplasts per ml, based on hemacytometer count.

For each filamentous fungal transformation, a 200 μl aliquot of protoplast suspension was added to a 15 ml test tube and incubated at 50° C. for 1 min then rapidly cooled on ice. Following a 5 min incubation at room temperature, 20 μl of PCR-amplified pCa-BG or pCoY-BG DNA (containing the plant viral promoter, β-glucosidase coding sequence and the pyr4 selectable marker) was added, along with 20 μl 0.2 M ammonium aurintricarboxylate (Sigma-Aldrich, St. Louis, Mo.) and 50 μl PEG buffer (60% polyethylene glycol 4000; 50 mM $CaCl_2$; 10 mM Tris-HCl, pH 7.5) and mixed well. The tube was heat-shocked again at 50° C. for 1 min, quickly cooled on ice, then incubated at room temperature for 20 min. Another 1.5 ml of PEG buffer was then added and mixed thoroughly by carefully rotating the tube. After a final 5 min incubation at room temperature, 5 ml of ice cold STC was added to the tube and mixed by inversion. The sample was then centrifuged (10 min, 3300×g, 4° C.) and the resulting pellet was suspended in approximately 500 μl of ice cold STC. A soft agar overlay technique was used to plate the transformation suspension onto selective media (TMM) osmotically stabilized with 0.6 M KCl. Plates were incubated at 30° C. Colonies of transformants were typically visible after 5-6 days.

5.4. Example 4

Identification of 5' UTR for *Trichoderma Reesei* Glyceraldehyde-3-Phosphate Dehydrogenase (gpd) Gene This example describes the mapping of 5' untranslated sequence in the *Trichoderma reesei* gpd gene.

In order to determine the approximate 5'UTR transcript initiation point, nested forward primers were designed within the 5' upstream region of the gpd gene. Standard PCR with each of these primers paired with a gpd coding sequence reverse primer was conducted on both cDNA (variable) and gDNA (control) sample templates for the *Trichoderma reesei* strain MCG80. Reverse-Transcriptase PCR (RT-PCR) was used to amplify the 5' UTR from the gpd gene from *Trichoderma reesei* RNA. Total RNA was extracted from *Trichoderma reesei* MCG80 culture using RNeasy Plant Mini Kit (Qiagen, Valencia, Calif.) and was used as template for RT-PCR/cDNA synthesis using Verso cDNA synthesis kit (Thermo Fisher Scientific, Fremont, Calif.) and subsequent PCR reactions. Genomic DNA (gDNA) was extracted from MCG80 culture using Masterpure Yeast DNA Purification Kit (Epicentre, Madison, Wis.) and was used as template for control PCR reactions.

The following primers were used.

TABLE 4

| SEQ ID NO: | Primer | Description | Sequence |
|---|---|---|---|
| 16 | 1 | 5' UTR forward primer, -34 from ATG start | GACTCACGCAA GCTCAATTCG |
| 17 | 2 | 5' UTR forward primer, -140 from ATG start | CCAGACTCTCCT GCGTCACCAAT |
| 18 | 3 | 5' UTR forward primer, -229 from ATG start | CTACAATCATCA CCACGATGCTCC |
| 19 | 4 | 5' UTR forward primer, -284 from ATG start | CGACATTCTCTC CTAATCACCAGC |
| 20 | 5 | 5' UTR forward | GCCGTGCCTACC TGCTTTAGTATT |

TABLE 4-continued

| SEQ ID NO: | Primer | Description | Sequence |
|---|---|---|---|
| | | primer, -402 from ATG start | |
| 21 | 6 | 5' UTR forward primer, -443 from ATG start | CCACTATCTCAG GTAACCAGGTAC |
| 22 | 7 | Reverse primer, +269 from ATG start | GTCTCGCTCCAC TTGATGTTGGCA |

The following forward and reverse primer combinations were run with both cDNA and gDNA templates.

Reaction #1 cDNA template with primer 1+primer 7
Reaction #2 cDNA template with primer 2+primer 7
Reaction #3 cDNA template with primer 3+primer 7
Reaction #4 cDNA template with primer 4+primer 7
Reaction #5 cDNA template with primer 5+primer 7
Reaction #6 cDNA template with primer 6+primer 7
Reaction #7 gDNA template with primer 1+primer 7
Reaction #8 gDNA template with primer 2+primer 7
Reaction #9 gDNA template with primer 3+primer 7
Reaction #10 gDNA template with primer 4+primer 7
Reaction #11 gDNA template with primer 5+primer 7
Reaction #12 gDNA template with primer 6+primer 7

The PCR reactions were prepared in 25 μl volumes containing the following: 9.5 μl water, 12.5 μl Taq polymerase mix, 1 μl each of the specified forward and reverse primer (1 μM), and 1 μl of the appropriate template DNA. The following thermal cycling steps were carried out: a cycle at 95° C. for 5 minutes, followed by 30 cycles of three steps consisting of 95° C. for 30 seconds, followed by 55° C. for 30 second, followed by 72° C. for 1 minutes, and ending with a 7 minute cycle at 72° C. 10 μl of each reactions were run on a 1% agarose gel. Bands were excised and purified using a Zymo Research Gel Extraction Kit (Zymo Research, Irvine, Calif.). The resulting fragments were cloned into pCR4—TOPO using a TOPO cloning for sequencing kit (Invitrogen, Carlsbad, Calif.) following the manufacturer's protocol. Individual clones were submitting for full length insert sequencing.

Results. As shown in FIG. 4, cDNA reaction banding patterns were compared to the counterpart reaction for the gDNA control. In this way, banding patterns would indicate that the standard PCR reaction for the nested set falls off between −229 and −284 bp upstream of the ATG start site. The genomic reaction banding pattern forms a steady nested pattern progression which is not seen for the cDNA sample set. Due to possible intron sites present in the gDNA template, the first three lanes for cDNA and corresponding gDNA reactions may not match exactly in size. Based on the observed banding patterns and sequence data results, indications are that the 5'UTR initiation site for the *Trichoderma reesei* MCG80 strain gpd transcript is between −229 and −284 bp upstream of the ATG start site. The appropriate bands, based on the upward nested banding pattern alone, were selected for excision. The sequence of the 5' UTR gpd fragments used to construct expression cassettes is as follows.

TABLE 5

| SEQ ID NO: | Description | Sequence |
|---|---|---|
| 4 | 100 bP gpd 5'UTR | CCTCCTCCCT CTCTCCCTCT CGTTTCTTCC TAACAAACAA CCACCACCAA AATCTCTTTG GAAGCTCACG ACTCACGCAA GCTCAATTCG CAGATACAAA |
| 5 | 150 bP gpd 5'UTR | AGCTACCCCG CCAGACTCTC CTGCGTCACC AATTTTTTTC CCTATTTACC CCTCCTCCCT CTCTCCCTCT CGTTTCTTCC TAACAAACAA CCACCACCAA AATCTCTTTG GAAGCTCACG ACTCACGCAA GCTCAATTCG CAGATACAAA |
| 6 | 200 bP gpd 5'UTR | ACGATGCGGC TTCTGTTCGC CTGCCCCTCC TCCCACTCGT GCCCTTGACG AGCTACCCCG CCAGACTCTC CTGCGTCACC AATTTTTTTC CCTATTTACC CCTCCTCCCT CTCTCCCTCT CGTTTCTTCC TAACAAACAA CCACCACCAA AATCTCTTTG GAAGCTCACG ACTCACGCAA GCTCAATTCG CAGATACAAA |

5.5. Example 5

Construction of a Vector Containing an Expression Cassette Including A CaMV 35S Promoter, A 5' Untranslated Region (5' UTR), and the Protein Coding Sequence For *Cochliobolus Heterostrophus* β-Glucosidase This example describes the construction of expression cassettes comprising a CaMV 35S promoter, a 5' UTR from CaMV or from the *Trichoderma reesei* gpd gene, and the protein coding sequence for *Cochliobolus heterostrophus* β-glucosidase, and a CBHI terminator as the 3' UTR.

The DNA fragments of CaMV promoter linked to a 5'UTR were generated using an 'overlapping PCR' strategy and then cloned into the pCa vector. 5' UTR sequence from gpd was amplified from pWG, a plasmid derived from pW described above incorporating the native gpd promoter from *Trichoderma reesei*. The plasmid pCa provided the template DNA for the CaMV 35S promoter.

5' UTR sequences used to generate expression cassettes is as follows for CaMV S1 5'UTR: GTACCGCTGA AATCACCAAT CTCTCTCTAC AAATCTATCT CTCTCTATTT CTC (SEQ ID NO: 3), and as provided in Table 4 in Example 4 above for each of the 5' UTR from gpd.

Construction of a fragment containing a CaMV 35 promoter and CaMV S1 5' UTR. Pairs of primers were used to amplify CaMV 35S promoter sequences from the pCa vector and designed to generate overlapping sequence with the 5' UTR sequence of native CaMV S1) as shown below.

TABLE 6

| SEQ ID NO: | Description | Sequence |
| --- | --- | --- |
| 23 | pCa forward primer with PacI site | CACCATTAATTAAGTCAAAGATTCAAATAGAGGACCTAACA |
| 24 | pCaMV3'-S1 reverse primer | TGTAGAGAGA GATTGGTGAT TTCAGCGGTA CCGTGTTCTCT CCAAATGAAA TGAA |
| 25 | S1-Spe reverse primer | CACCAACTAG TGAGAAATAG AGAGAGATAG ATTTGTAGAG AGAGATTGGT GATTTCAGC |

To generate a fragment containing the 5' UTR from the native CaMV transcript (or CaMV S1 5' UTR), the pCa vector was used a template in a first round of PCR, with primers corresponding to SEQ ID NO:23 and 24. The DNA generated in this reaction was then used as a template for a second round of PCR, using a forward primer corresponding to SEQ ID NO:23 and a reverse primer designed to amplify the CaMV S1 5' UTR (SEQ ID NO:25), generating a fragment containing the CaMV promoter and the native CaMV S1 5' UTR.

Construction of a fragment containing a CaMV 35S promoter and gpd 5' UTR. The CaMV35S promoter was amplified from pCa-BG DNA, described in Example 1 above, using the following primers.

TABLE 7

| SEQ ID NO: | Description | Sequence |
| --- | --- | --- |
| 23 | pCa forward primer with PacI site | CACCATTAATTAAGTCAAAGATTCAAATAGAGGACCTAACA |
| 26 | pCa overlap-100 bp gpd 5' UTR reverse primer | AGAGGGAGAGAGGGAGGAGGCGTGTTCTCTCCAAATGAAATG |
| 27 | pCa overlap-150 bp gpd 5' UTR reverse primer | GAGAGTCTGGCGGGGTAGCTCGTGTTCTCTCCAAATGAAATG |
| 28 | pCa overlap-200 bp gpd 5' UTR reverse primer | GCGAACAGAAGCCGCATCGTCGTGTTCTCTCCAAATGAAATG |

The gpd 5' UTR fragments were amplified from pWG, containing a fragment of the gpd gene upstream of the translational start cloned into pW (described in Example 1 above), using a forward primer specific to the 5' UTR fragment (100 bp, 150 bp or 200 bp, respectively) and the same reverse primer. Together, each primer pair was designed to generate a 5' UTR fragment that included overlap in sequence with the CaMV 35S promoter fragments, such that resulting CaMV 35S and gpd 5'UTR fragments could readily be ligated together for subcloning. Forward and reverse primers used to amplify the 100 bp, 150 bp, and 200 bp gpd 5' UTR were as follows.

TABLE 8

| SEQ ID NO: | Description | Sequence |
| --- | --- | --- |
| 29 | pCa overlap-100 bp gpd 5' UTR forward | CATTTCATTTGGAGAGAACACGCCTCCTCCCTCTCTCCCTCT |

TABLE 8-continued

| SEQ ID NO: | Description | Sequence |
|---|---|---|
| 30 | pCa overlap-150 bp gpd 5' UTR forward | CATTTCATTTGGAGAGAACACGAGCTACCCCGCCAGACTCTC |
| 31 | pCa overlap-200 bp gpd 5' UTR forward | CATTTCATTTGGAGAGAACACGACGATGCGGCTTCTGTTCGC |
| 32 | pWG-SpeI site reverse primer | CACCAACTAGTTTTGTATCTGCGAATTGAGCTTGCGTGA |

PCR reactions were performed by using AccuPrime pfx DNA polymerase (Invitrogen, 12344) and following manufacturer's protocol. The primer sets were used in series to add the specified 5' UTR sequences to the initial CaMV 35S promoter fragments. The resulting DNA fragments containing promoter and 5' UTR sequences were subcloned as follows into the pCa vector. The PCR products were purified by Zymoclean Gel DNA Recovery kit (Zymo Research, D4001). Purified PCR fragments and pCa DNA were digested with restriction enzymes Pac I (New England Biolabs R0547S) and Spe I(New England Biolabs R0133S) to create cloning ends. pCa vector and PCR insert were ligated by T4 DNA ligase (Roche, 11 635 379 001) and transformed E. coli competent cells XL1-Blue (Stratagene, 200236) following manufactures' instructions, generating vectors containing expression cassettes comprising a CaMV 35S promoter, a 5' UTR sequence, a protein coding sequence, and a terminator sequence. The vectors, schematically represented in FIG. 5, are denominated as follows: pCa-S1 for an expression cassette containing a 5'UTR from the CaMV S1 5'UTR (FIG. 5A), and pCa-100 (FIG. 5B), pCa-150 (FIG. 5C), and pCa-200 (FIG. 5D) for expression cassettes containing a 100 nucleotide sequence (SEQ ID NO:4), 150 nucleotide sequence (SEQ ID NO:5), and 200 nucleotide sequence (SEQ ID NO:6), of the 5'UTR of the gpd gene, respectively.

Transformation. Each of the expression cassettes was transformed into *Trichoderma reesei* according to the protocol described above in Example 3. Specifically, protoplasts of the strain *Trichoderma reesei* MCG80 pyr-4—were prepared as described above, and used in transformations with each one of the eight constructs described in the previous section containing a UTR sequence downstream of the viral promoter in each case, but upstream of the β-glucosidase coding sequence.

5.6. Example 6

**β-glucosidase Activity in *Trichoderma Reesei* Transformants Containing CaMV-5'UTR or CaMV Expression Cassettes**

This example provides a demonstration of β-glucosidase activity in *Trichoderma reesei* transformants containing CaMV-5'UTR or CaMV expression cassettes, showing the increase in enzyme activity in *Trichoderma reesei* strains transformed with a vector comprising a full expression cassette as compared to vectors containing a promoter operably linked to a protein coding sequence.

Growth Conditions and Media. For analysis of expression among *Trichoderma reesei* transformants, individual isolates displaying the pyr4+ phenotype were inoculated into the wells of a 96-well plate containing 0.2 ml/well ACM (Aspergillus Complete Medium) or CM (Complete Medium). Complete medium was as follows: 0.5% yeast extract, 1% glucose (filtered), 0.2% casamino acids (sterile), 7 mM KCl; 11 mM $KH_2PO_4$; 70 mM $NaNO_3$; 2 mM $MgSO_4$; 77 µM $ZnSO_4$; 178 µM $H_3BO_3$; 25 µM $MnCl_2$; 18 µM $FeSO_4$; 7.1 µM $CoCl_2$; 6.4 µM $CuSO_4$; 6.2 µM $Na_2MoO_4$; 134 µM $Na_2EDTA$; 1 mg/ml riboflavin; 1 mg/ml thiamine; 1 mg/ml nicotinamide; 0.5 mg/ml pyridoxine; 0.1 mg/ml pantothenic acid; 2 µg/ml biotin; 1 mM uridine (filtered). Plates were incubated in a stationary, humidified incubator at 30° C. for 7 days. Following incubation, the fluid underneath the filamentous fungal mats was harvested and assayed for β-glucosidase activity as follows.

β-Glucosidase Activity Assay. The β-glucosidase activities of harvested fluid samples were measured using 4MU-G (Sigma product#M3633) as substrate in an assay performed on liquid handling robot. The method is as follows: 100 µl aliquots of reaction buffer (0.5 mM 4MU-G in 100 mM NaOAc, pH5.0) were transferred into each well of a 96-well flat-bottom microplate (Corning Inc., Costar, black polystyrene) using a Titertek Multidrop mircroplate dispenser (Titertek, Huntsville, Ala.). The reactions were then initiated by the addition of 40 aliquots of the harvested fluid samples, transferred and mixed on a VPrep pipetting system (Agilent, Santa Clara, Calif.). The microplate containing the reaction buffer and samples was then incubated at room temperature for 3 minutes. After incubation, the reaction was stopped by the addition of 100 µl aliquots of stop buffer (400 mM Sodium Carbonate, pH10.0) into each well using a Titertek Multidrop microplate dispenser. The fluorescence of each well was then measured as relative units at 360/465 nm (denoted RFU) using an Ultra Microplate Reader (Tecan Group Ltd., Mannedorf Switzerland). The relative fluorescence of the transformants were then compared to the RFU signals of the control, untransformed strains.

Results. β-glucosidase activity from transformants containing pCa-BG was not significantly above background. FIG. 6A-B provides bar charts of β-glucosidase activity in *Trichoderma reesei* transformants bearing a 5' untranslated region from the native *Trichoderma reesei* gpd gene, or the native CaMV viral gene in addition to the CaMV promoter relative to control, untransformed *Trichoderma reesei* tested in ACM (FIG. 6A) or CM (FIG. 6B). The constructs containing expression cassettes bearing a CaMV promoter, a 5' untranslated region from the native *Trichoderma reesei* gpd gene, or the native CaMV viral gene showed expression significantly above the background level of activity generated by the native *Trichoderma reesei* β-glucosidase activity. Thus, expression cassettes comprising a plant viral promoter, a 5' UTR operable in the host strain, a protein coding sequence, and a terminator sequence comprising a 3' UTR result in efficient translation of the transcript leading to increased activity of a protein.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A nucleic acid sequence comprising an expression cassette, said expression cassette comprising, operably linked in a 5' to 3' direction: (a) a plant viral promoter that is constitutively expressed in plant cells wherein the plant viral promoter is a cauliflower mosaic virus (CaMV) promoter, a Commelina yellow mottle virus ("CoYMV") promoter, a Figwort Mosaic Virus (FMV) promoter, or a cassava vein mosaic virus (CsVMV) promoter; (b) a 5' untranslated region ("UTR") operable in filamentous fungi; (c) a first polypeptide coding sequence comprising a start codon and a stop codon; and (d) a 3' UTR.

2. The nucleic acid of claim 1, wherein the plant viral promoter is a CaMV 35S promoter.

3. The nucleic acid of claim 2, wherein the a CaMV 35S promoter comprises the nucleotide sequence of SEQ ID NO:1.

4. The nucleic acid of claim 1, wherein the plant viral promoter is a CoYMV promoter.

5. The nucleic acid of claim 4, wherein the CoYMV promoter comprises the nucleotide sequence of SEQ ID NO:2.

6. The nucleic acid of claim 1, wherein the 5' UTR is from the *Trichoderma reesei* glyceraldehyde-3-phosphate dehydrogenase gene.

7. The nucleic acid of claim 6, wherein the 5' UTR comprises the nucleotide sequence of SEQ ID NO:4.

8. The nucleic acid of claim 7, wherein the 5' UTR comprises the nucleotide sequence of SEQ ID NO:5.

9. The nucleic acid of claim 1, wherein the 5' UTR is a CaMV S1 5' UTR.

10. The nucleic acid of claim 6, wherein the CaMV S1 5' UTR comprises the nucleotide sequence of SEQ ID NO:3.

11. The nucleic acid of claim 1, wherein the 3' UTR comprises a polyadenylation signal.

12. The nucleic acid of claim 1, which further comprises between the first polypeptide coding sequence and the 3' UTR an internal ribosome entry site ("IRES") and a second polypeptide coding sequence.

13. The nucleic acid of claim 1, wherein the first polypeptide is a filamentous fungal polypeptide.

14. The nucleic acid of claim 1, wherein the first polypeptide is a *Trichoderma reesei* polypeptide.

15. The nucleic acid of claim 1, wherein the first polypeptide is a yeast, mammalian or bacterial polypeptide.

16. The nucleic acid of claim 1, wherein the first polypeptide is a beta-glucosidase.

17. The nucleic acid of claim 16, wherein the beta-glucosidase comprises the amino acid sequence of SEQ ID NO:34.

18. The nucleic acid of claim 1, wherein the first polypeptide comprises a signal sequence.

19. A vector comprising the nucleic acid of claim 1.

20. The vector of claim 19 which comprises an origin of replication.

21. The vector of claim 19 which comprises a selectable marker.

22. The vector of claim 21, wherein the selectable marker is an antibiotic resistance gene or an auxotrophic marker.

23. A filamentous fungal cell comprising a recombinant expression cassette, said expression cassette comprising in operable linkage: (a) a plant viral promoter that is constitutively expressed in plant cells wherein the plant viral promoter is a cauliflower mosaic virus (CaMV) promoter, a Commelina yellow mottle virus ("CoYMV") promoter, a Figwort Mosaic Virus (FMV) promoter, or a cassava vein mosaic virus (CsVMV) promoter; (b) a 5' untranslated region ("UTR") operable in filamentous fungi; (c) a first polypeptide coding sequence comprising a start codon and a stop codon; and (d) a 3' UTR.

24. The filamentous fungal cell of claim 23, wherein the plant viral promoter is a CaMV 35S promoter.

25. The filamentous fungal cell of claim 24, wherein the a CaMV 35S promoter comprises the nucleotide sequence of SEQ ID NO:1.

26. The filamentous fungal cell of claim 23, wherein the plant viral promoter is a CoYMV promoter.

27. The filamentous fungal cell of claim 26, wherein the CoYMV promoter comprises the nucleotide sequence of SEQ ID NO:2.

28. The filamentous fungal cell of claim 23, wherein the 5' UTR and/or the 3' UTR is native to the filamentous fungal cell.

29. The filamentous fungal cell of claims 23, wherein the 5' UTR is from the *Trichoderma reesei* glyceraldehyde-3-phosphate dehydrogenase gene.

30. The filamentous fungal cell of claim 29, wherein the 5' UTR comprises the nucleotide sequence of SEQ ID NO:4.

31. The filamentous fungal cell of claim 29, wherein the 5' UTR comprises the nucleotide sequence of SEQ ID NO:5.

32. The filamentous fungal cell of claim 23, wherein the 5' UTR is a CaMV S1 5' UTR.

33. The filamentous fungal cell of claim 32, wherein the CaMV S1 5' UTR comprises the nucleotide sequence of SEQ ID NO:3.

34. The filamentous fungal cell of claim 23, wherein the 3' UTR comprises a polyadenylation signal.

35. The filamentous fungal cell of claim 23, wherein the first protein coding sequence is native to the filamentous fungal cell.

36. The filamentous fungal cell of claim 23, wherein the expression cassette further comprises between the first polypeptide coding sequence and the 3' UTR an internal ribosome entry site ("IRES") and a second polypeptide coding sequence.

37. The filamentous fungal cell of claim 36, wherein the second protein coding sequence is 5' to the first protein coding sequence.

38. The filamentous fungal cell of claim 36, wherein the second protein coding sequence is 3' to the first protein coding sequence.

39. The filamentous fungal cell of claim 23, wherein the first polypeptide is a filamentous fungal polypeptide.

40. The filamentous fungal cell of claim 37, wherein the first polypeptide is endogenous to the filamentous fungal cell.

41. The filamentous fungal cell of claim 37, wherein the first polypeptide is heterologous to the filamentous fungal cell.

42. The filamentous fungal cell of claim 23, wherein the first polypeptide is a yeast, mammalian or bacterial polypeptide.

43. The filamentous fungal cell of claim 23, wherein the first polypeptide coding sequence encodes a .beta.-glucosidase.

44. The filamentous fungal cell of claim 43, wherein the .beta.-glucosidase comprises the amino acid sequence of SEQ ID NO:34.

45. The filamentous fungal cell of claim 23, wherein the first polypeptide coding sequence encodes a polypeptide comprising a signal sequence.

46. The filamentous fungal cell of claim 23, wherein the expression cassette is in the filamentous fungal cell genome.

47. The filamentous fungal cell of claim 23, wherein the expression cassette is on an extragenomic vector.

48. The filamentous fungal cell of claim 47, wherein the extragenomic vector contains a selectable marker.

49. The filamentous fungal cell of claim 23 which is a species of *Acremonium, Aspergillus, Emericella, Fusarium, Humicola, Mucor, Myceliophthora, Neurospora, Penicillium, Scytalidium, Thielavia, Chrysosporium, Phanerochaete, Tolypocladium,* or *Trichoderma*.

50. The filamentous fungal cell of claim 49 which is of the species *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum, Phanerochaete chrysosporium, Phlebia radiate, Pleurotus eryngii, Thielavia terrestris, Trichoderma harzianum, Trichoderma longibrachiatum, Trichoderma reesei,* or *Trichoderma viride*.

51. The filamentous fungal cell of claim 23, wherein the first protein coding sequence encodes a protein comprising a signal sequence.

52. The filamentous fungal cell of claim 23, wherein the first protein is a cellulase, a hemicellulase or an accessory protein.

53. The filamentous fungal cell of claim 51, wherein the cellulase, hemicellulase or accessory protein comprises a signal sequence.

54. The filamentous fungal cell of claim 36, wherein the second protein is a cellulase, a hemicellulase or an accessory protein.

55. The filamentous fungal cell of claim 54, wherein the cellulase, hemicellulase or accessory protein comprises a signal sequence.

56. A method for producing a recombinant polypeptide, comprising culturing the filamentous fungal cell of claim 23 under conditions that result in expression of the first polypeptide.

57. The method of claim 56, further comprising recovering the first polypeptide.

58. The method of claim 57, further comprising purifying the first polypeptide.

59. A method for producing a secreted polypeptide, comprising culturing the filamentous fungal cell of claim 45 under conditions that result in expression and secretion of the first polypeptide.

60. The method of claim 59, further recovering the first polypeptide.

61. The method of claim 60, wherein the first polypeptide is recovered from the culture medium.

62. The method of claim 61, further comprising purifying the first polypeptide.

63. A method for producing a cellulase composition, comprising culturing the filamentous fungal cell of claim 51 under conditions that result in expression of the first protein.

64. The method of claim 63, further comprising recovering a cellulase composition.

65. The method of claim 64, wherein the cellulase composition is a fermentation broth in which the filamentous fungal cells are cultured.

66. A method for producing a cellulase composition, comprising culturing the filamentous fungal cell of claim 53 under conditions that result in expression of the second protein.

67. The method of claim 66, further comprising recovering a cellulase composition.

68. The method of claim 66, wherein the cellulase composition is a fermentation broth in which the filamentous fungal cells are cultured.

69. A method for saccharifying biomass, comprising: (a) producing a cellulase composition by the method of claim 63; (b) treating biomass with said cellulase composition, thereby producing saccharifying said biomass.

70. The method of claim 69, further comprising recovering fermentable sugars from said saccharified biomass.

71. The method of claim 70, wherein the fermentable sugars comprise disaccharides.

72. The method of claim 70, wherein the fermentable sugars comprise monosaccharides.

73. The method of claim 69, wherein said biomass is corn stover, bagasses, sorghum, giant reed, elephant grass, miscanthus, Japanese cedar, wheat straw, switchgrass, hardwood pulp, softwood pulp, crushed sugar cane, energy cane, or Napier grass.

74. The method of claim 69, further comprising, prior to step (b), pretreating the biomass.

75. A method for producing a fermentation product, comprising: (a) producing a cellulase composition by the method of claim 57; (b) treating biomass with said cellulase composition, thereby producing fermentable sugars; and (c) culturing a fermenting microorganism in the presence of the fermentable sugars produced in step (b) under fermentation conditions, thereby producing a fermentation product.

76. The method of claim 75, wherein said fermentable sugars comprise disaccharides.

77. The method of claim 75, wherein the fermentable sugars comprise monosaccharides.

78. The method of claim 75, wherein the fermentation product is ethanol.

79. The method of claim 75, further comprising, prior to step (b), pretreating the biomass.

80. The method of claim 75, wherein said fermenting microorganism is a bacterium or a yeast.

81. The method of claim 75, wherein said fermenting microorganism is a bacterium selected from *Zymomonas mobilis, Escherichia coli* and *Klebsiella oxytoca*.

82. The method of claim 75, wherein said fermenting microorganism is a yeast selected from *Saccharomyces cerevisiae, Saccharomyces uvarum, Kluyveromyces fragilis, Kluyveromyces lactis, Candida pseudotropicalis*, and *Pachysolen tannophilus*.

83. The method of claim 75, wherein said biomass is corn stover, bagasses, sorghum, giant reed, elephant grass, miscanthus, Japanese cedar, wheat straw, switchgrass, hardwood pulp, softwood pulp, crushed sugar cane, energy cane, or Napier grass.

* * * * *